(12) United States Patent
Hassanzadeh Ghassabeh et al.

(10) Patent No.: US 11,155,607 B2
(45) Date of Patent: Oct. 26, 2021

(54) SERUM ALBUMIN BINDING AGENTS

(71) Applicant: VIB VZW, Ghent (BE)

(72) Inventors: Gholamreza Hassanzadeh Ghassabeh, Sint-Genesius-Rode (BE); Steve Schoonooghe, Kessel-Lo (BE); Erik Depla, Destelbergen (BE)

(73) Assignee: VIB VZW, Ghent (BE)

( * ) Notice: Subject to any disclaimer, the term of this patent is extended or adjusted under 35 U.S.C. 154(b) by 0 days.

(21) Appl. No.: 16/631,360

(22) PCT Filed: Jul. 17, 2018

(86) PCT No.: PCT/EP2018/069443
§ 371 (c)(1),
(2) Date: Jan. 15, 2020

(87) PCT Pub. No.: WO2019/016237
PCT Pub. Date: Jan. 24, 2019

(65) Prior Publication Data
US 2020/0255504 A1    Aug. 13, 2020

(30) Foreign Application Priority Data
Jul. 19, 2017   (EP) .................................. 17182200.0

(51) Int. Cl.
*C07K 16/18*   (2006.01)
(52) U.S. Cl.
CPC .......... *C07K 16/18* (2013.01); *C07K 2317/24* (2013.01); *C07K 2317/31* (2013.01); *C07K 2317/565* (2013.01); *C07K 2317/567* (2013.01); *C07K 2317/94* (2013.01)

(58) Field of Classification Search
None
See application file for complete search history.

(56) References Cited

FOREIGN PATENT DOCUMENTS

| WO | 2008096158 A2 | 8/2008 |
| WO | 2014037419 A1 | 3/2014 |
| WO | 2014191904 A1 | 12/2014 |

OTHER PUBLICATIONS

Dave et al., Fab-dsFv: A bispecific antibody format with extended serum half-life through albumin binding, MABS, vol. 8, No. 7, Aug. 17, 2016, pp. 1319-1335.
Holt, et al., "anti-serum albumin domain antibodies for extending the half-lives of short lived drugs," Protein Engineering, Design Selection: Peds. May 2008, vol. 21, No. 5, May 1, 2008, pp. 283-288.
PCT International Search Report and Written Opinion; Application No. PCT/EP2018/069443, filed of Jul. 17, 2018, dated Oct. 22, 2018, 10 pages.

*Primary Examiner* — Adam Weidner
(74) *Attorney, Agent, or Firm* — Patent Law Works, LLP

(57) ABSTRACT

The present invention relates to polypeptides comprising an immunoglobulin variable domain, binding with high affinity to serum albumin for increasing the half-life of therapeutic agents and compositions, in particular for therapeutic agents comprising multispecific immunoglobulin variable domains. Also provided herein are methods for the production of polypeptides comprising serum albumin binding immunoglobulin variable domains of the present invention.

16 Claims, 6 Drawing Sheets
Specification includes a Sequence Listing.

Figure 1

SERUM ALBUMIN BINDING AGENTS

FIELD OF THE INVENTION

The present invention relates to polypeptides comprising an immunoglobulin variable domain, binding with high affinity to serum albumin for increasing the half-life of therapeutic agents and compositions, in particular for therapeutic agents comprising multispecific immunoglobulin variable domains. Also provided herein are methods for the production of polypeptides comprising serum albumin binding immunoglobulin variable domains of the present invention.

BACKGROUND

A growing number of protein therapeutics is being developed, such as monoclonal antibodies, antibody fragments and vaccines, hormones, growth factors, cytokines, coagulation factors, enzymes, fusion proteins and other proteins, many of them—except for whole antibodies and Fc-fusion proteins—possessing a molecular mass below 50 kDa, being rapidly cleared by renal filtration and degradation resulting in a short plasma half-life. To assure therapeutic effect, this drawback requires high and frequent dosing with as a consequence considerable negative side effects, which is especially detrimental for patients with frequent systemic administrations of therapeutics like, for example, insulin to diabetics, or interferon drugs in patients suffering from multiple sclerosis. The investigation of half-life extension strategies finds increasing attention by the biotech and pharmaceutical industry because of the obvious therapeutic as well as economic benefits.

Some plasma proteins such as serum albumin and IgG molecules possess an extraordinary long half-life in the range of 2-4 weeks (Kontermann, 2009) because of a recycling mechanism through the neonatal Fc receptor (FcRn, Brambell receptor) (Chaudhury et al., 2003; Roopenian and Akilesh, 2007). Albumin and IgGs taken up by cells, bind to the FcRn in a pH-dependent manner in the acidic environment of the early endosome. This binding diverges albumin and IgG from degradation in the lysosomal compartment and redirects them to the plasma membrane, where they are released back into the blood plasma due to the neutral pH. This mechanism has been exploited to extend half-life of proteins, for example, through fusion to albumin or the Fc-region of IgG. Serum albumin can also be engaged in half-life extension through modules with the capacity to non-covalently interact with albumin. In these approaches, an albumin-binding moiety is either conjugated or genetically fused to the therapeutic protein. A wide range of different moieties have been employed including molecules with intrinsic affinity for albumin but also other molecules such as peptides, antibody fragments, alternative scaffolds, and small chemicals generated and selected to exhibit albumin binding activity.

Camelids produce functional antibodies devoid of light chains (Hamers-Casterman et al., 1993) with their single N-terminal domain, a VHH, also referred to as Nanobody®, binding antigen without requiring domain pairing. Such VHHs present interesting therapeutic possibilities owing to their small size, high stability, ease of modification by genetic fusions and good production levels in microorganisms. However, the small size of VHHs is also a therapeutic disadvantage because of their rapid clearance from circulation when administered to patients. On the other hand, this also offers opportunities for coupling them to half-life extension molecules, or coupling to specific drugs (e.g. formation of antibody-drug conjugates) or tracers. A variety of coupling methods are described in the art (e.g. especially applied in the field of the modification of monoclonal antibodies) and these technologies focus for example on conjugation via primary amine groups (Lysine residues and N-terminus) or via cysteines, by acylation or alkylation, respectively.

In mice and rat, the natural half-life of serum albumin is approximately 1.5-2.5 days, and different serum albumin binders have been shown to exhibit a comparable half-life, i.e. approximately 2 days. A Nanobody® specific for mouse albumin was fused to two antagonistic anti-EGFR Nanobody® generating a bispecific, trivalent molecule, and increased the half-life from 1 to 44 hours and efficiently delayed outgrowth of EGFR-positive tumors in animal models (Roovers et al., 2007). With respect to pre-clinical studies, the metabolic physiology of the rat is however closer to humans than of mice, which makes the rat a better species to study the pharmacokinetic/pharmacodynamic characteristics and human toxicology of drugs. In addition, the larger size of rats as compared to mice allows sophisticated surgical manipulations, and larger volume of blood/CSF and tissue for optimal experimental readouts. Genetically modified rat models now also enable drug efficacy and safety studies, thereby making rat inherently more translational than mouse in preclinical studies to do safety studies in the same strain and species as efficacy. As studied for instance by Hoefman et al. (2015), the half-life of albumin binders in different species, such as rodents, primates and human is critical to allow optimal dosing and reach the desired exposure in efficacy studies, and allowing more reliable cross-species exposure prediction. Hence, it is clearly of importance to not only rely on the half-life of a serum albumin binding protein in its therapeutic target species, i.e. human, but also for albumin in each animal species of interest in a pre-clinical development setting. It would be advantageous to find serum albumin binding agents or polypeptides not only with sufficiently high affinity to human albumin to extend the half-life of a therapeutic protein, but also to identify those serum albumin binding agents with the highest affinity or longest half-life in frequently used testing animals, such as rodents, to increase the success rate and translatability of pre-clinical results.

VHHs are advantageous for therapeutic targeting, due to their small size as monovalent or as multivalent or multi-specific structures, and due to the possibility of extending therapeutic protein half-life through fusion with a VHH targeting serum albumin antigen. Another example of a serum albumin binding VHH was provided by Ablynx N.V. (WO 2004/041865, and WO2006/122787) describing Nanobody® directed against serum albumin, and in particular against human serum albumin, that can be linked to other (therapeutic) proteins (such as one or more other Nanobody® directed against a desired target) in order to increase the half-life of said (therapeutic) protein in a patient.

So in conclusion, serum albumin binding VHHs would be of interest to increase the half-life of therapeutic proteins, possibly also a VHH, as fusion partner of the serum albumin binding VHH, not only in human, but also in the test species, to allow more extensive pre-clinical data gathering prior to the larger studies in non-human primates or follow-up clinical studies. Such a serum albumin binding VHH would allow more reliable and easier development of novel therapeutics. And, since VHHs were also shown to be useful in for instance tumor targeting as antibody-drug conjugates (Fang et al., 2016), it would be desirable to identify specific VHHs which can be conjugated without encumbering the binding function to serum albumin, and ideally a combination of said two features to increase efficient R&D of novel therapeutics. Finally, the VHHs to be developed for therapeutic use, should also be suitable with regards to their biochemical properties.

SUMMARY OF THE INVENTION

The invention relates to the generation and characterization of a novel VHH that binds serum albumin, and which upon mutation of a glycosylation site that was present in one of the complementarity determining regions (CDRs) surprisingly retained its serum albumin binding affinity, and moreover demonstrated very high affinity for rat serum albumin. Furthermore, said novel serum albumin binding VHH has high antibody-drug conjugate (ADC) potential because after coupling the introduced lysine and a conjugate, its serum albumin binding affinity, hence in vivo half life extension capacity, was retained, although the serine to lysine mutation was made in CDR 1.

A first aspect of the invention relates to a polypeptide comprising an immunoglobulin variable domain (IVD), wherein said IVD binds to serum albumin with high affinity, as determined by BioLayer Interferometry, wherein said IVD comprises an amino acid sequence following the common structure FR1-CDR1-FR2-CDR2-FR3-CDR3-FR4, and wherein the 3 complementarity determining regions (CDRs) are represented by the CDR1, CDR2, and CDR3 regions as present in SA1_S30K VHH (SEQ ID NO:4) or a humanized variant thereof (h1 to h4: SEQ ID NOs: 8-11; FIG. 5). In FIG. 1, the annotation of CDR regions in view of SA1_S30K is shown. In particular, said CDR regions are determined by the Chothia, AbM, MacCallum, or IMTG method. The specific affinity for serum albumin is in one embodiment human serum albumin, and alternatively rat, mouse and cyno serum albumin. In one embodiment, the polypeptide comprises the IVD wherein the CDRs are defined by the amino acid sequence of SEQ ID NO:1 for CDR1; the amino acid sequence of SEQ ID NO:2 for CDR2; and the amino acid sequence of SEQ ID NO:3 for CDR3.

In a further embodiment, the polypeptide of the invention comprises an IVD wherein the CDRs are defined as described herein, and wherein the FR3 region is defined by the FR3 region of SA1_S30K, or the FR3 amino acid sequence of a humanized variant of SA1_S30K, wherein the FR3 region is defined according to the annotation applied (FIG. 1), and wherein position 73 and 74 of the IVD can be any amino acid, wherein position 78 can be V or L, wherein position 79 is H or Y, and/or position 82b is T or S (according to Kabat numbering). In one embodiment, the FR3 sequence is defined according to the annotation of AbM, corresponding to SEQ ID NO:18, and wherein the position 74 is S, position 79 is Y, and/or position 82b is S.

In another embodiment, said polypeptide comprising a serum albumin binding IVD, relates to an IVD comprising the amino acid sequence of SA1_S30K (SEQ ID NO:4) or a humanized variant thereof.

Another embodiment relates to the polypeptide comprising said IVD of the invention, wherein the FR3 amino acid sequence at position 79 is Tyrosine (Y) and/or at position 82b is Serine (S) (according to Kabat numbering). In one embodiment, the polypeptide comprises an IVD comprising the amino acid sequence with said FR3 amino acid sequence, which is a humanized variant of SA1_S30K (or SEQ ID NO:4). In a specific embodiment, the polypeptide of the invention comprises the humanized variant of SA1_S30K h1 to h7 as depicted in SEQ ID NO:8, SEQ ID NO:9, SEQ ID NO:10, SEQ ID NO:11, SEQ ID NO:15, SEQ ID NO:16, or SEQ ID NO:17, respectively. More specifically, SA1_S30K may be alternatively humanized by at least one substitution of, or said humanized variants may further comprise at least one additional substitution of: position 1 to E or D, position 5 to V, position 14 to P, position 73 to any amino acid, position 74 to any amino acid, position 78 to L, or position 108 to L (according to Kabat numbering; also presented in FIG. 5 ('alternative h')). In a particular embodiment, said polypeptide comprising said serum albumin binding IVD is an IVD conjugate, wherein said IVD is coupled to said conjugate via the lysine residue present in CDR1, more particular as shown at position 1 of SEQ ID NO:1. In a more particular embodiment, said conjugate is a drug.

One embodiment relates to said polypeptide of the present invention, for use to increase the half-life of a therapeutic moiety. An alternative embodiment relates to a therapeutic agent with increased serum half-life, characterized in that said agent comprises the polypeptide of the invention and a therapeutic moiety, wherein the serum half-life of the therapeutic agent is longer as compared to the agent without the polypeptide of the invention. Another embodiment applies the polypeptide of the invention, or the therapeutic agent comprising the polypeptide of the invention, for use as a medicament.

In a second aspect, the invention relates to a multispecific construct, which comprises said polypeptide comprising said serum albumin binding immunoglobulin variable domain (IVD), and at least one therapeutic moiety. Another embodiment relates to said multispecific construct, wherein the therapeutic moiety comprises an IVD or a fragment thereof. In a more particular embodiment, the therapeutic moiety comprises an immunoglobulin single variable domain, or a fragment thereof. Even more particular, in one embodiment said polypeptide is linked to the at least one therapeutic moiety via a linker or spacer.

Another aspect of the invention provides a nucleotide sequence or nucleic acid that encodes the polypeptide, or the multispecific construct of the present invention. Other embodiments relate to a host cell comprising the polypeptide, the multispecific construct, or the nucleotide sequence or nucleic acid according to the invention.

Further embodiments disclose a pharmaceutical composition comprising at least one polypeptide, multispecific construct, or therapeutic agent of such as described herein, and optionally at least one pharmaceutically acceptable carrier, diluent or excipient.

A final aspect of the invention relates to a method to produce a serum albumin binding polypeptide comprising the steps of i) recombinant expression of said polypeptide, said multispecific construct, or said nucleotide sequence or nucleic acid, in a suitable expression system, and ii) isolation or purification of said expressed serum albumin binding polypeptide to obtain said serum albumin binding polypeptide comprising said albumin binding IVD.

DESCRIPTION OF THE FIGURES

The drawings described are only schematic and are non-limiting. In the drawings, the size of some of the elements may be exaggerated and not drawn on scale for illustrative purposes.

FIG. 1: Amino acid sequence of serum albumin binding SA1_S30K VHH and CDR annotation.

Kabat numbering of the amino acids is shown, and CDRs are displayed based on contact Analysis and binding site topography as described in MacCallum et al., J. Mol. Biol. (1996) 262, 732-745. The regions corresponding to alternative CDR annotations (AbM, Chothia, Kabat, IMGT) are also displayed.

Figure 2:
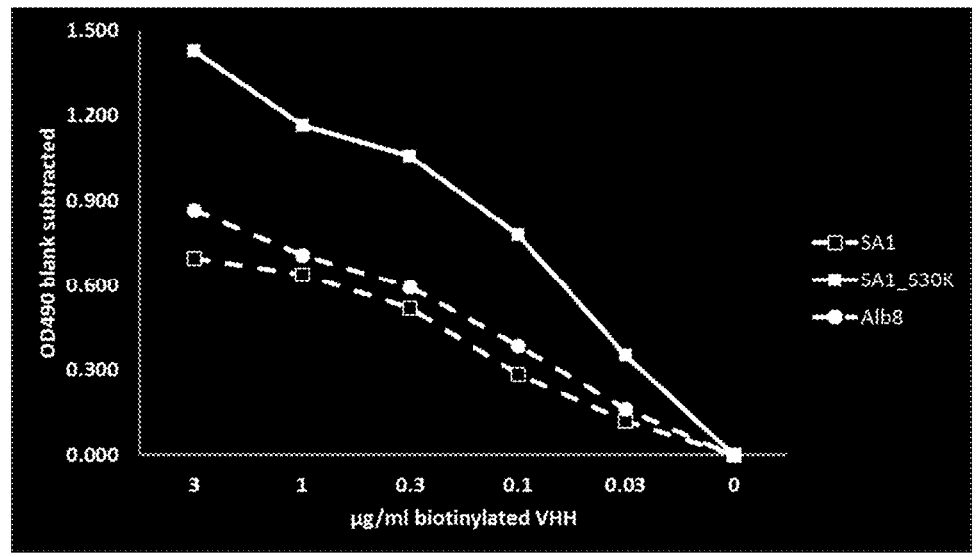

FIG. 2: ELISA showing binding of biotinylated SA1, Alb8, and SA1_S30K to human serum albumin.

Figure 3:
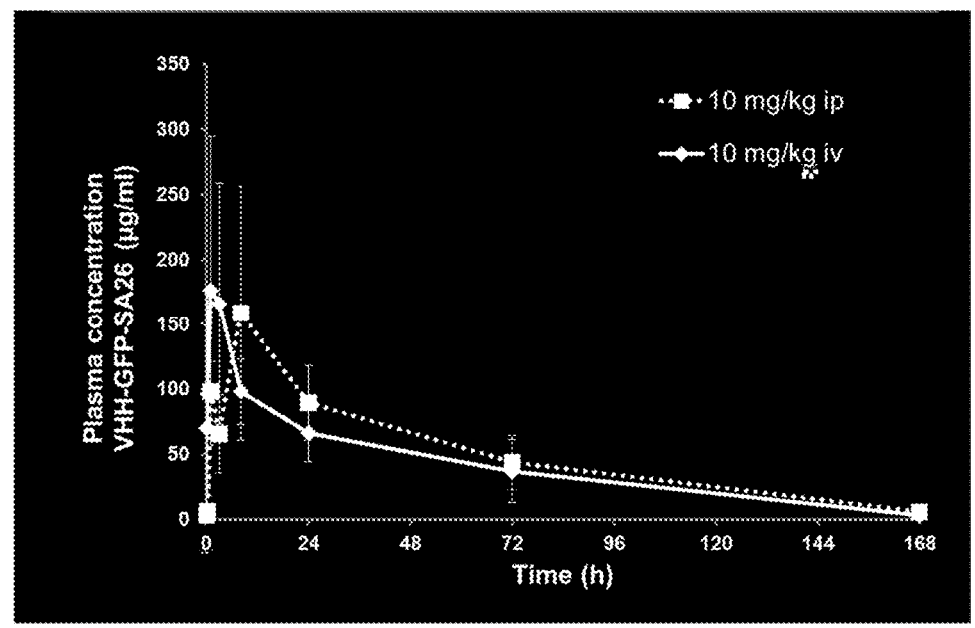

FIG. 3: Pharmacokinetics profile of SA1_S30K VHH in mice.
Plasma concentrations of VHH-GFP-SA1_S30K upon intravenous (iv) or intraperitoneal (ip) injection at 10 mg/kg in mice.

Figure 4:
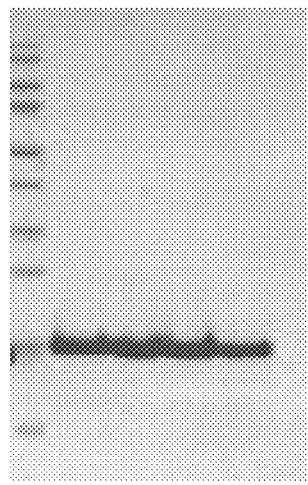

FIG. 4: SDS-PAGE analysis of purified SA1_S30K humanized VHH variants.
Coomassie stained gel of 5 µg loaded Nb. From left to right: Thermo Pageruler pre-stained marker, purified SA1_S30K h1, h2, h3, h4 VHH (SEQ ID NO: 8, 9, 10, 11, resp. with an additional His-tag).

Figure 5:
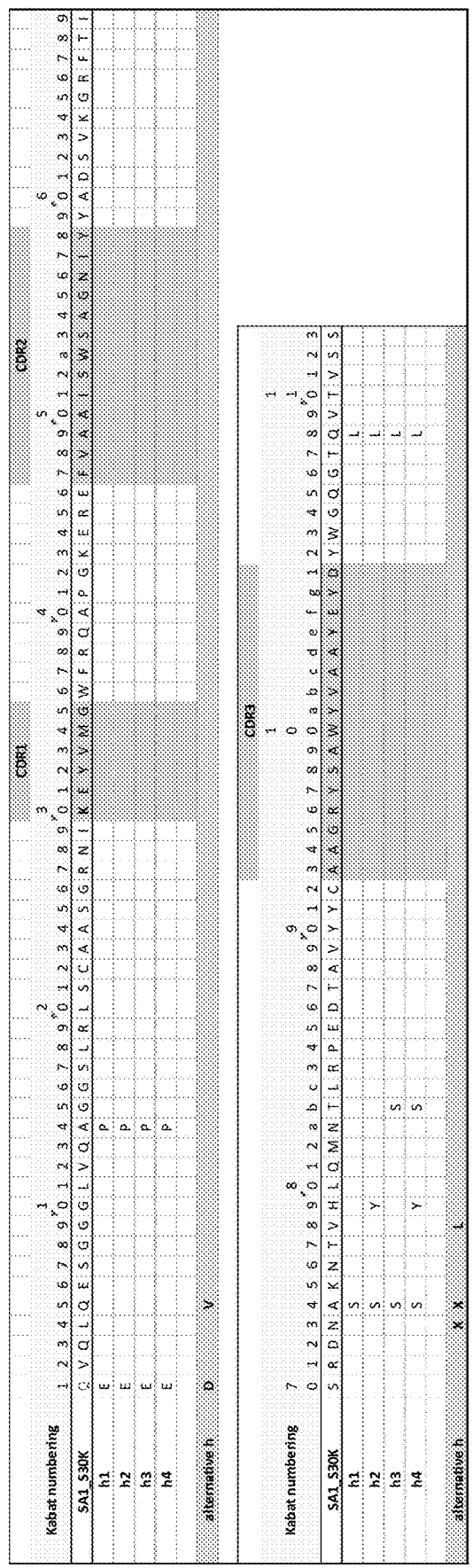

FIG. 5: Alignment of SA1_S30K VHH and humanization variants.
CDR regions are shown in grey, as annotated in FIG. 1. The amino acid sequence of SA1_S30K is numbered according to Kabat. The amino acid substitutions in the humanized variants SA1_S30K_h1 to h4 (h1, h2, h3, and h4, corresponding to SEQ ID NOs: 8-11, resp.) is shown in alignments with the sequence of SA1_S30K. Furthermore, possible alternate humanization positions/substitutions are shown in the line indicated as 'alternative h', with any combination of substitutions presented in this line together with any of the sequences presented above (SA1_S30K, h1 to h4) comprising a (further) humanized variant of SA1_S30K (SEQ ID NO:4) or of SA1_S30K_h1 (SEQ ID NO:8), SA1_S30K_h2 (SEQ ID NO:9), SA1_S30K_h3 (SEQ ID NO:10), SA1_S30K_h4 (SEQ ID NO:11).

Figure 6:
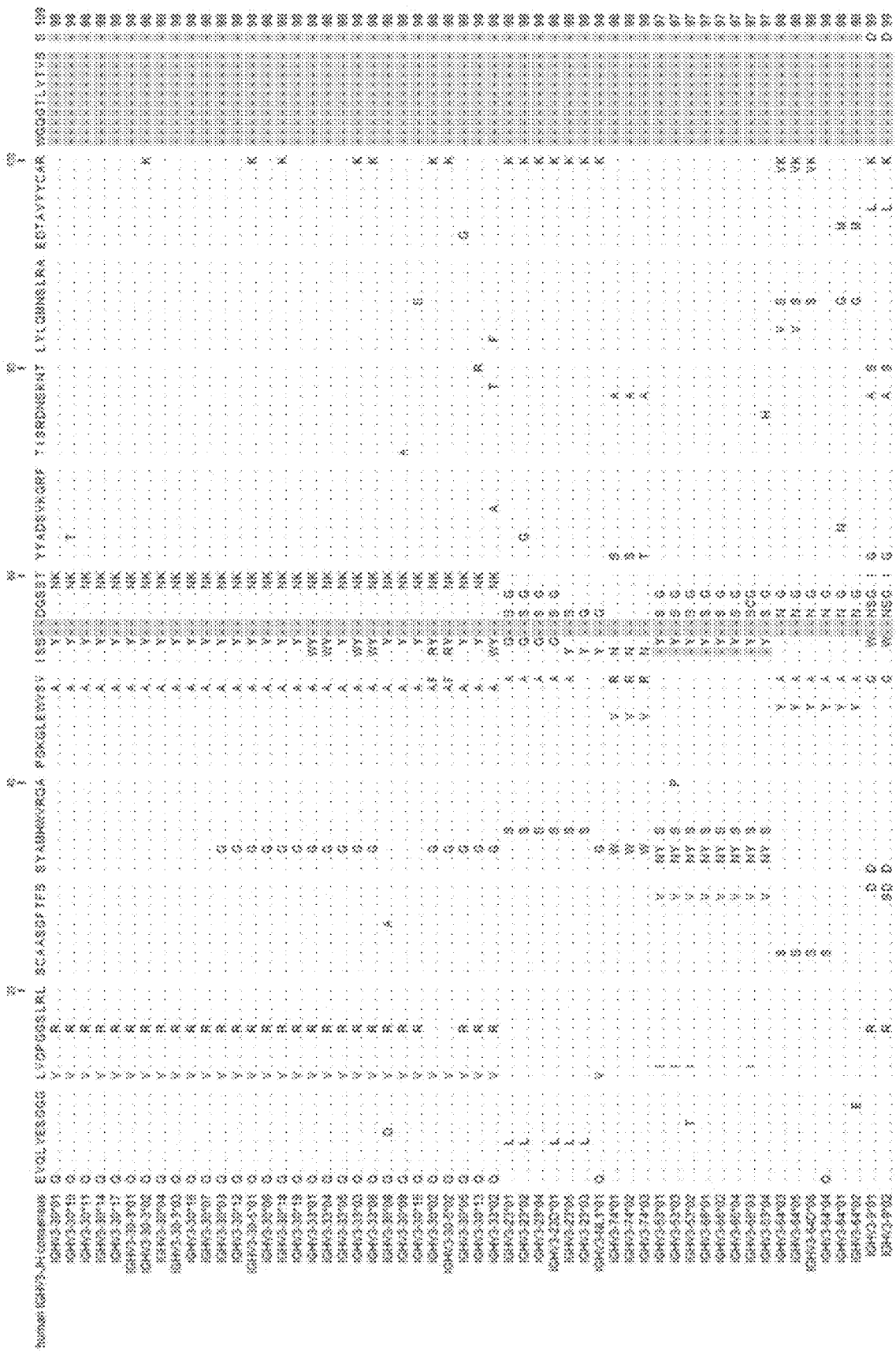
Figure 6:
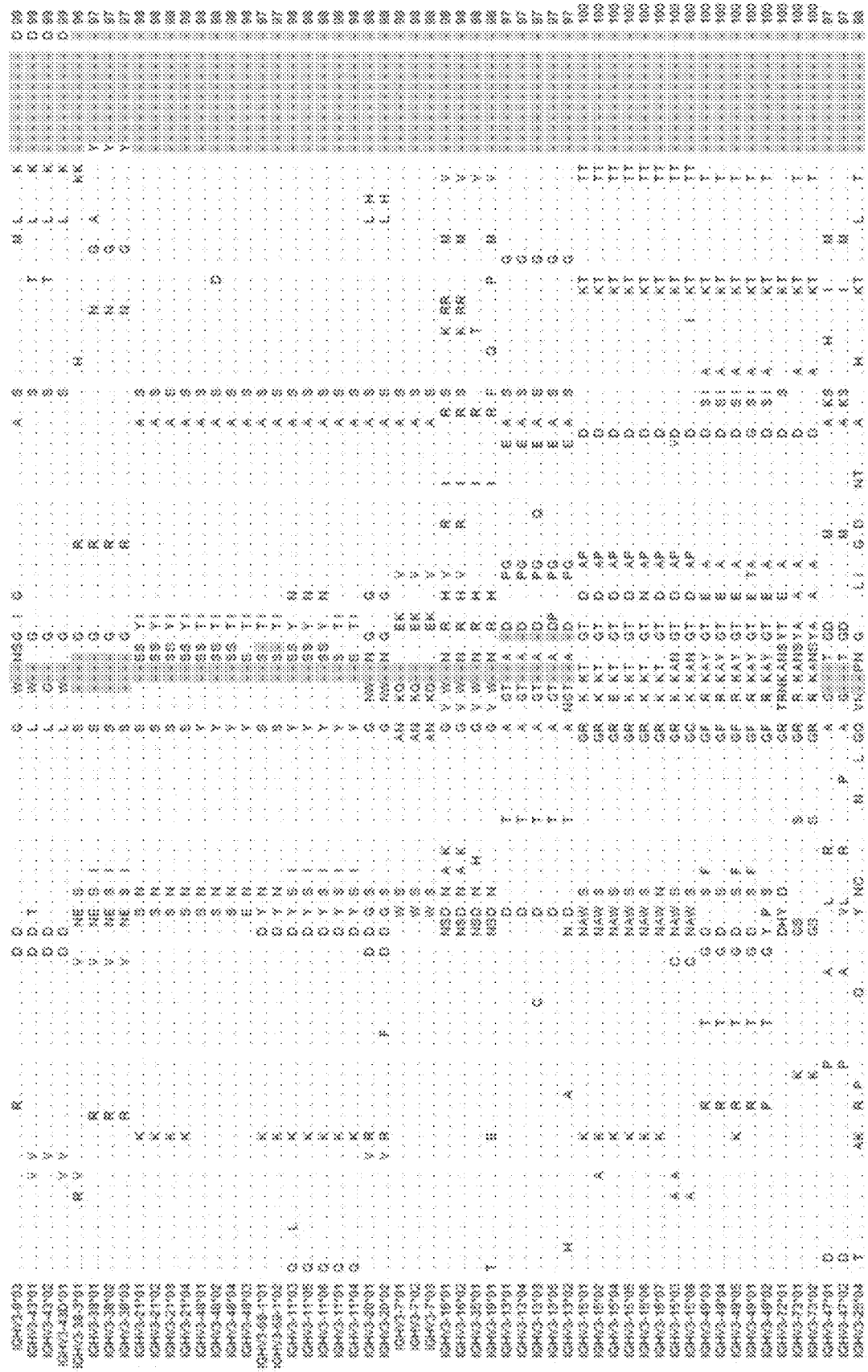

FIG. 6: Alignment of human IGHV3 germline alleles compared to a human reference consensus sequence.
Alleles of IGHV3-30, IGHV3-33, IGHV3-NL1, IGHV3-9, IGHV3-25, IGHV3-43 and IGHV3-20 are compared herein (corresponding to the amino acid sequences SEQ ID NO:19 to 157 in this application). Sequences are found in the IMGT database, or in The Immunoglobulin FactsBook (Lefranc and Lefranc, San Diego, Calif., Academic Press, 2001).

DETAILED DESCRIPTION TO THE INVENTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, N.Y. (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

Definitions

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. "Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. "Gene" as used here includes both the promoter region of the gene as well as the coding sequence. It refers both to the genomic sequence (including possible introns) as well as to the cDNA derived from the spliced messenger, operably linked to a promoter sequence.

The terms "protein", "polypeptide", "peptide" are interchangeably used further herein to refer to a polymer of amino acid residues (shown in three- or one-letter code herein, with each 3- or 1-letter denominating an amino acid residue in accordance with the standard code) and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes post-translational modifications of the polypeptide, such as glycosylation, phosphorylation and acetylation. A "protein domain" is a distinct functional and/or structural unit in a protein. Usually a protein domain is responsible for a particular function or interaction, contributing to the overall role of a protein. Domains may exist in a variety of biological contexts, where similar domains can be found in proteins with different functions. By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation. By "isolated" or "purified" is meant material that is substantially or essentially free from components that normally accompany it in its native state. For example, an "isolated polypeptide" or "purified polypeptide", as used herein, refers to a polypeptide, which has been purified from the molecules which flank it in a naturally-occurring state, e.g., a protein comprising a serum albumin binding IVD protein which has been removed from the molecules present in the production host that are adjacent to said isolated protein. Such an isolated or pure protein can also be generated by amino acid chemical synthesis or by generated by recombinant production.

The term "fusion protein" refers to proteins created by joining two or more distinct (poly-)peptides or proteins, preferably head-to-tail (i.e., N-terminus to C-terminus or vice versa), resulting in a single protein with functional properties derived from each of the original proteins. The term "fused to", as used herein, refers, in particular, to genetic fusion, e.g., by recombinant DNA technology. A fusion can be made directly between two proteins, or can be made via a linker.

The term "detectable label or tag", as used herein, refers to detectable labels or tags allowing the detection and/or isolation, purification and/or immobilization of the isolated or purified (poly-)peptides described herein, and is meant to include any labels/tags known in the art for these purposes. Particularly preferred are affinity tags, such as chitin binding protein (CBP), maltose binding protein (MBP), glutathione-S-transferase (GST), poly(His) (e.g., 6xHis or His6), Strep-tag®, Strep-tag II® and Twin-Strep-tag®; solubilization tags, such as thioredoxin (TRX), poly(NANP) and SUMO; chromatography tags, such as a FLAG-tag; epitope tags, such as V5-tag, myc-tag and HA-tag; fluorescent labels or tags (i.e., fluorochromes/-phores), such as fluorescent proteins (e.g., GFP, YFP, RFP etc.) and fluorescent dyes (e.g., FITC, TRITC, coumarin and cyanine); luminescent labels or tags, such as luciferase; and (other) enzymatic labels (e.g., peroxidase, alkaline phosphatase, beta-galactosidase, urease or glucose oxidase).

Also included are combinations of any of the foregoing labels or tags. The isolated (poly-)peptide may, for example, be fused or conjugated to a half-life extension module, or may function as a half-life extension module itself. Such modules are known to a person skilled in the art and include, for example, albumin, an albumin-binding domain, an Fc region/domain of an immunoglobulins, an immunoglobulin-binding domain, an FcRn-binding motif, and a polymer. Particularly preferred polymers include polyethylene glycol (PEG), hydroxyethyl starch (HES), hyaluronic acid, polysialic acid and PEG-mimetic peptide sequences. Modifications preventing aggregation of the isolated (poly-)peptides are also known to the skilled person and include, for example, the substitution of one or more hydrophobic amino acids, preferably surface-exposed hydrophobic amino acids, with one or more hydrophilic amino acids. In one embodiment, the isolated (poly-)peptide or the immunogenic variant thereof or the immunogenic fragment of any of the foregoing, comprises the substitution of up to 10, 9, 8, 7, 6, 5, 4, 3 or 2, preferably 5, 4, 3 or 2, hydrophobic amino acids, preferably surface-exposed hydrophobic amino acids, with hydrophilic amino acids. Preferably, other properties of the isolated (poly-)peptide, e.g., its immunogenicity, are not compromised by such substitution.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified", "mutant" or "variant" refers to a gene or gene product that displays modifications in sequence, post-translational modifications and/or functional properties (i.e., altered characteristics) when compared to the wild-type gene or gene product. It is noted that naturally occurring mutants can be isolated; these are identified by the fact that they have altered characteristics when compared to the wild-type gene or gene product.

The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. A "substitution", or "mutation" as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity.

"Binding" means any interaction, be it direct or indirect. A direct interaction implies a contact between the binding partners. An indirect interaction means any interaction whereby the interaction partners interact in a complex of more than two compounds. The interaction can be completely indirect, with the help of one or more bridging molecules, or partly indirect, where there is still a direct contact between the partners, which is stabilized by the additional interaction of one or more compounds. By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody" as used herein, refers to an immunoglobulin (Ig) molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel β-strands arranged in two β-sheets, optionally stabilized by a conserved disulphide bond.

The term "immunoglobulin variable domain" (abbreviated as "IVD") as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) (IVDs) that confer specificity to an antibody for the antigen by carrying the antigen-binding site.

The term "immunoglobulin single variable domain" (abbreviated as "ISVD"), equivalent to the term "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen. In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs. As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody. For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody® (as defined herein, and including but not limited to a VHH); other single variable domains, or any suitable fragment of any one thereof. In particular, the immunoglobulin single variable domain may be a Nanobody® (as defined herein) or a suitable fragment thereof. Note: Nanobody®, Nanobodies® and Nanoclone® are registered trademarks of Ablynx N.V. For a general description of Nanobodies®, reference is made to the further description below, as well as to the prior art cited herein, such as e.g. described in WO2008/020079. Numbering of IVD or ISVD sequences are described herein according to Kabat nomenclature, unless explicitly mentioned otherwise.

"VHH domains", also known as VHHs, VHH domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al (1993) Nature 363: 446-448). The term "VHH domain" has been chosen to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHHs and Nanobody®, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As described in these references, Nanobody® (in particular VHH sequences and partially humanized Nanobody®) can in particular be characterized by the presence of one or more "Hallmark residues" in one or more of the framework sequences. A further description of the Nanobody®, including humanization and/or camelization of Nanobody®, as well as other modifications, parts or fragments, derivatives or "Nanobody® fusions", multivalent constructs (including some non-limiting examples of linker sequences) and different modifications to increase the half-life of the Nanobody® and their preparations can be found e.g. in WO 08/101985 and WO 08/142164.

"Domain antibodies", also known as "Dabs", "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans. It should also be noted that single variable domains can be derived from certain species of shark (for example, the so-called "IgNAR domains", see for example WO 05/18629).

Immunoglobulin single variable domains such as Domain antibodies and Nanobody® (including VHH domains and humanized VHH domains), can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996). The process of designing/selecting and/or preparing a polypeptide, starting from an immunoglobulin single variable domain such as a Domain antibody or a Nanobody®, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats for instance to avoid glycosylation will be clear to the skilled person based on the disclosure herein.

Immunoglobulin single variable domains such as Domain antibodies and Nanobody® (including VHH domains) can be subjected to humanization, i.e. increase the degree of sequence identity with the closest human germline sequence. In particular, humanized immunoglobulin single variable domains, such as Nanobody® (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined further herein). Potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person. Also, based on what is described before, (the framework regions of) an immunoglobulin single variable domain, such as a Nanobody® (including VHH domains) may be partially humanized or fully humanized.

A "serum albumin binding agent", or "serum albumin binding polypeptide", as used herein, is a protein-based agent capable of specific binding to serum albumin. In various embodiments, the serum albumin binding agent may bind to the full-length and/or mature forms and/or isoforms and/or splice variants and/or fragments and/or any other naturally occurring or synthetic analogs, variants or mutants of serum albumin. In various embodiments, the serum albumin binding agent of the invention may bind to any forms of serum albumin, including monomeric, dimeric, trimeric, tetrameric, heterodimeric, multimeric and associated forms. In an embodiment, the serum albumin binding agent binds to the monomeric form of serum albumin. In an embodiment, the present serum albumin binding polypeptide comprises immunoglobulin variable domain with an antigen binding site that comprises three complementarity determining regions (CDR1, CDR2 and CDR3). In an embodiment said antigen binding site recognizes one or more epitopes present on serum albumin. In various embodiments, the serum albumin binding agent comprises a full length antibody or fragments thereof. In an embodiment, the serum albumin binding agent comprises a single domain antibody or an immunoglobulin single variable domain (ISVD). In a specific embodiment, the serum albumin binding agent binds to serum albumin of rat (Uniprot P02770, SEQ ID NO: 14). In a specific embodiment, the serum albumin binding agent binds to serum albumin of mouse (Uniprot P07724, SEQ ID NO: 13). In a specific embodiment, the serum albumin binding agent binds to human serum albumin (Uniprot P02768, SEQ ID NO:12).

The terms "subject", "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, fish, reptiles, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). However, it will be understood that the aforementioned terms do not imply that symptoms are present. The term "treatment" or "treating" or "treat" can be used interchangeably and are defined by a therapeutic intervention that slows, interrupts, arrests, controls, stops, reduces, or reverts the progression or severity of a sign, symptom, disorder, condition, or disease, but does not necessarily involve a total elimination of all disease-related signs, symptoms, conditions, or disorders. The term "medicament", as used herein, refers to a substance/composition used in therapy, i.e., in the prevention or treatment of a disease or disorder. According to the invention, the terms "disease" or "disorder" refer to any pathological state, in particular to the diseases or disorders as defined herein.

DETAILED DESCRIPTION

In a first aspect, the invention relates to a polypeptide comprising an immunoglobulin variable domain (IVD), wherein said IVD specifically binds to serum albumin. Said IVD particularly comprising a general structure of FR1-CDR1-FR2-CDR2-FR3-CDR3-FR4. In various embodiments, the serum albumin binding polypeptide of the invention provides binding affinity for the full-length and/or mature forms and/or isoforms and/or splice variants and/or fragments and/or monomeric and/or dimeric and/or tetrameric forms and/or any other naturally occurring or synthetic analogs, variants, or mutants (including monomeric and/or dimeric and/or tetrameric forms) of human serum albumin (Uniprot P02768, SEQ ID NO:12), and may be described by the equilibrium dissociation constant ($K_D$). In various embodiments, the serum albumin binding polypeptide of the invention provides binding affinity for the full-length and/or mature forms and/or isoforms and/or splice variants and/or fragments and/or monomeric and/or dimeric and/or tetrameric forms and/or any other naturally occurring or synthetic analogs, variants, or mutants (including monomeric and/or dimeric and/or tetrameric forms) of rat serum albumin (Uniprot P02770, SEQ ID NO:14), and may be described by the equilibrium dissociation constant ($K_D$). In various embodiments, the serum albumin binding polypeptide of the invention provides binding affinity for the full-length and/or mature forms and/or isoforms and/or splice variants and/or fragments and/or monomeric and/or dimeric and/or tetrameric forms and/or any other naturally occurring or synthetic analogs, variants, or mutants (including monomeric and/or dimeric and/or tetrameric forms) of mouse serum albumin (Uniprot PP07727, SEQ ID NO:13), and may be described by the equilibrium dissociation constant ($K_D$).

SEQ ID NO: 12 depicts the amino acid sequence of full-length human serum albumin (Uniprot P02768).
SEQ ID NO: 12: human serum albumin (Uniprot P02768)
MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQRLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVESKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKC

CTESLVNRRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL

SEQ ID NO: 13 depicts the amino acid sequence of full-length mouse serum albumin (Uniprot P07724).
SEQ ID NO: 13: mouse serum albumin (Uniprot P07724)
MKWVTFLLLLFVSGSAFSRGVFRREAHKSEIAHRYNDLGEQHFKGLVLIA

FSQYLQKCSYDEHAKLVQEVTDFAKTCVADESAANCDKSLHTLFGDKLCA

IPNLRENYGELADCCTKQEPERNECFLQHKDDNPSLPPFERPEAEAMCTS

FKENPTTFMGHYLHEVARRHPYFYAPELLYYAEQYNEILTQCCAEADKES

CLTPKLDGVKEKALVSSVRQRMKCSSMQKFGERAFKAWAVARLSQTFPNA

DFAEITKLATDLTKVNKECCHGDLLECADDRAELAKYMCENQATISSKLQ

TCCDKPLLKKAHCLSEVEHDTMPADLPAIAADFVEDQEVCKNYAEAKDVF

LGTFLYEYSRRHPDYSVSLLLRLAKKYEATLEKCCAEANPPACYGTVLAE

FQPLVEEPKNLVKTNCDLYEKLGEYGFQNAILVRYTQKAPQVSTPTLVEA

ARNLGRVGTKCCTLPEDQRLPCVEDYLSAILNRVCLLHEKTPVSEHVTKC

CSGSLVERRPCFSALTVDETYVPKEFKAETFTFHSDICTLPEKEKQIKKQ

TALAELVKHKPKATAEQLKTVMDDFAQFLDTCCKAADKDTCFSTEGPNLV

TRCKDALA

-continued

SEQ ID NO: 14 depicts the amino acid sequence of
full-length rat serum albumin (Uniprot P02770).
SEQ ID NO: 14: rat serum albumin (Uniprot P02770)
MKWVTFLLLLFISGSAFSRGVFRREAHKSEIAHRFKDLGEQHFKGLVLIA

FSQYLQKCPYEEHIKLVQEVTDFAKTCVADENAENCDKSIHTLFGDKLCA

IPKLRDNYGELADCCAKQEPERNECFLQHKDDNPNLPPFQRPEAEAMCTS

FQENPTSFLGHYLHEVARRHPYFYAPELLYYAEKYNEVLTQCCTESDKAA

CLTPKLDAVKEKALVAAVRQRMKCSSMQRFGERAFKAWAVARMSQRFPNA

EFAEITKLATDVTKINKECCHGDLLECADDRAELAKYMCENQATISSKLQ

ACCDKPVLQKSQCLAEIEHDNIPADLPSIAADFVEDKEVCKNYAEAKDVF

LGTFLYEYSRRHPDYSVSLLLRLAKKYEATLEKCCAEGDPPACYGTVLAE

FQPLVEEPKNLVKTNCELYEKLGEYGFQNAVLVRYTQKAPQVSTPTLVEA

ARNLGRVGTKCCTLPEAQRLPCVEDYLSAILNRLCVLHEKTPVSEKVTKC

CSGSLVERRPCFSALTVDETYVPKEFKAETFTFHSDICTLPDKEKQIKKQ

TALAELVKHKPKATEDQLKTVMGDFAQFVDKCCKAADKDNCFATEGPNLV

ARSKEALA

The invention relates to the polypeptide which comprises the serum albumin binding IVD that comprises an amino acid sequence with 3 complementarity determining regions (CDRs), characterized by the CDR1, CDR2 and CDR3 region of SA1_S30K (SEQ ID NO:4), or of a humanized variant thereof such as h1, h2, h3, h4 (SEQ ID NO:8-11).

SEQ ID NO: 4 depicts the amino acid sequence of
the full length SA1_S30K VHH.
SEQ ID NO: 4: SA1_S30K
QVQLQESGGGLVQAGGSLRLSCAASGRNIKEYVMGWFRQAPGKEREFVAA

ISWSAGNIYYADSVKGRFTISRDNAKNTVHLQMNTLRPEDTAVYYCAAGR

YSAWYVAAYEYDYWGQGTQVTVSS

In one embodiment, said polypeptide comprising a serum albumin binding IVD has high affinity for rat serum albumin, wherein said affinity is at least 1000-fold higher, or a $K_D$ that is at least 1000-fold lower, than for the benchmark (Alb8 anti-Serum albumin Nanobody® of Ablynx N.V.; see Examples), and preferably said affinity is at least 5000-fold higher, or said $K_D$ a 5000-fold lower than for the benchmark.

A particular embodiment provides that said IVD comprising protein binds rat serum albumin with a high affinity ($K_D$) of ≤40 pM. The term "affinity" refers to the degree to which an immunoglobulin, such as an antibody, binds to an antigen so as to shift the equilibrium of antigen and antibody toward the presence of a complex formed by their binding. Thus, where an antigen and antibody are combined in relatively equal concentration, an antibody of high affinity will bind to the available antigen so as to shift the equilibrium toward high concentration of the resulting complex. So binding affinity is the strength of the binding interaction between the IVD and the antigen, in this case serum albumin, and is typically measured and reported by the equilibrium dissociation constant ($K_D$), which is used to evaluate and rank order strengths of bimolecular interactions. The smaller the $K_D$ value, the greater the binding affinity of the ligand for its target. Measuring or determining binding affinity and dissociation constants can be done via BioLayer Interferometry (BLI), or by Surface Plasmon resonance (SPR), but also via for instance ELISA, gel-shift assays, pull-down assays, equilibrium dialysis, analytical ultracentrifugation, and spectroscopic assays. Another method to determine the affinity is via Isothermal titration calorimetry (ITC) for instance, which is a direct, label-free assay which measures the binding affinity between any two biomolecules that interact with each other, for example Ig/antigen binding, and can measure KD values in the millimolar and nanomolar range, as well as the binding stoichiometry and binding thermodynamics important in the characterization of intermolecular interactions. ITC is described as the "Gold Standard" of interaction analysis as it enables the study of a broad range of interactions and delivers highly quantitative KD values. Another embodiment relates to an immunoglobulin single variable domain (ISVD) binding to serum albumin, preferably to rat serum albumin with an affinity of ≤40 pM, as determined by Biolayer interferometry.

SEQ ID NO: 5 depicts the amino acid sequence of
the full length SA1 VHH.
SEQ ID NO: 5: SA1
QVQLQESGGGLVQAGGSLRLSCAASGRNISEYVMGWFRQAPGKEREFVAA

ISWSAGNIYYADSVKGRFTISRDNAKNTVHLQMNTLRPEDTAVYYCAAGR

YSAWYVAAYEYDYWGQGTQVTVSS

When comparing to the SA1 VHH, the one amino acid substitution in SA1_S30K increased the affinity to rat serum albumin by 20-fold, or at least by 10-fold. In addition, the mouse serum albumin binding of SA1_S30K also revealed to be of high affinity, with a $K_D$ value of ≤300 pM, which is at least 2-fold or at least 1.5-fold higher affinity as compared to the SA1 VHH. In comparison to the benchmark VHH, Alb8, both mouse and rat, but also cynomolgus monkey serum albumin bind with much higher affinity to the SA1_S30K, providing an opportunity to improve developmental and pre-clinical assets.

So in an alternative one embodiment, the polypeptide comprising an IVD with high affinity to rat serum albumin, is a polypeptide with an affinity of at least 1000-fold higher, or a $K_D$ of at least 1000-fold lower, than the rat serum albumin of the benchmark (Alb8 anti-Serum albumin Nanobody® of Ablynx N.V.), and preferably with affinity of at least 5000-fold higher than the rat serum albumin of the benchmark (Alb8 anti-Serum albumin Nanobody® of Ablynx N.V.).

Surprisingly, by introducing just one mutation, in order to remove a glycosylation site, and the mutation site being located in CDR1 at position 30 (FIG. 1), the affinity for human serum albumin could be retained, with a $K_D$ value of about 0.9 nM (Table 4), close to the affinity observed for SA1 and Alb8 controls, and moreover even a significant increase in binding affinity to rat and mouse serum albumin was observed for the SA1_S30K mutant variant. Rat and mouse serum albumin show a high homology in amino acid sequence of about 90% identity, and the homology between human and rat serum albumin is also quite high with an identity of 73%, which makes the finding of such increased affinity for rat serum albumin truly astonishing. This surprising feature has the advantage that many of the preclinical safety and efficacy studies done in rat and mouse can take profit from a longer half-life, as also seen in Example 7, where the PK in mouse resulted in a half-life of approx. 30 h, which is corresponding to the very high affinity reflected by the $K_D$ value.

In various embodiments, the protein comprises an IVD with an affinity ($K_D$) for binding to the full-length and/or mature forms and/or isoforms and/or splice variants and/or fragments and/or any other naturally occurring or synthetic analogs, variants, or mutants (including monomeric and/or dimeric and/or tetrameric forms) of rat serum albumin (Uniprot P02770, SEQ ID NO: 14) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

In other embodiments the protein comprises an IVD with an affinity ($K_D$) for binding to the full-length and/or mature forms and/or isoforms and/or splice variants and/or fragments and/or any other naturally occurring or synthetic analogs, variants, or mutants (including monomeric and/or dimeric and/or tetrameric forms) of mouse serum albumin (Uniprot P07724, SEQ ID NO:13) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

Moreover, in alternative embodiments, the protein comprises an IVD with an affinity ($K_D$) for binding to the full-length and/or mature forms and/or isoforms and/or splice variants and/or fragments and/or any other naturally occurring or synthetic analogs, variants, or mutants (including monomeric and/or dimeric and/or tetrameric forms) of human serum albumin (Uniprot P02768, SEQ ID NO:12) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM. Said human serum albumin binding affinity still being similar in the SA1_S30K variant VHH, which contains a lysine substitution, as compared to SA1, in its CDR1 (FIG. 1) was very unexpected, and additionally provides advantages to the invention, as discussed later below.

Moreover, in alternative embodiments, the protein comprises an IVD with an affinity (KD) for binding to the full-length and/or mature forms and/or isoforms and/or splice variants and/or fragments and/or any other naturally occurring or synthetic analogs, variants, or mutants (including monomeric and/or dimeric and/or tetrameric forms) of cynomolgus monkey serum albumin (Uniprot A2V924) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

Moreover, in alternative embodiments, the protein comprises an IVD with an affinity (KD) for binding to the full-length and/or mature forms and/or isoforms and/or splice variants and/or fragments and/or any other naturally occurring or synthetic analogs, variants, or mutants (including monomeric and/or dimeric and/or tetrameric forms) of rabbit serum albumin (Uniprot P49065) of at least about 10 µm, about 9 µM, about 8 µM, about 7 µM, about 6 µM, about 5 µM, about 5 µM, about 5 µM, about 5 µM, about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

Moreover, in alternative embodiments, the protein comprises an IVD with an affinity (KD) for binding to the full-length and/or mature forms and/or isoforms and/or splice variants and/or fragments and/or any other naturally occurring or synthetic analogs, variants, or mutants (including monomeric and/or dimeric and/or tetrameric forms) of horse serum albumin (Uniprot P35747) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

Moreover, in alternative embodiments, the protein comprises an IVD with an affinity (KD) for binding to the full-length and/or mature forms and/or isoforms and/or splice variants and/or fragments and/or any other naturally occurring or synthetic analogs, variants, or mutants (including monomeric and/or dimeric and/or tetrameric forms) of dog serum albumin (Uniprot P49822) of at least about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 5 nM, about 2.5 nM, about 1 nM, about 950 pM, about 900 pM, about 800 pM, about 700 pM, about 600 pM, about 500 pM, about 450 pM, about 400 pM, about 350 pM, about 300 pM, about 250 pM, about 200 pM, about 150 pM, about 100 pM, about 50 pM, about 30 pM, about 25 pM, about 20 pM, about 15 pM, about 10 pM, about 5 pM, or of at least about 1 pM.

Figure 1:
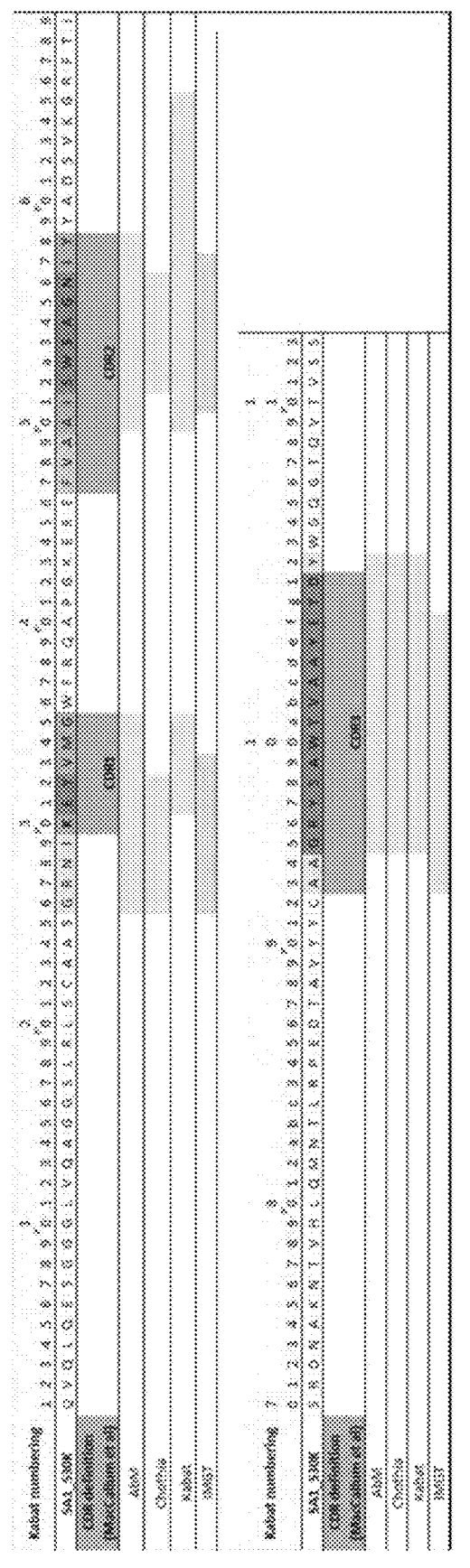

The invention relates to the polypeptide which comprises the serum albumin binding IVD that comprises an amino acid sequence with 3 complementarity determining regions (CDRs), characterized by the CDR1, CDR2 and CDR3 region of SA1_S30K (SEQ ID NO:4), or of a humanized variant thereof such as h1, h2, h3, h4 (SEQ ID NO: 8-11), wherein the CDR annotations in view of SA1S30K or its variants are depicted in FIG. 1. The MacCallum, AbM, Chothia or IMGT annotation is applicable to identify the CDR regions. Kabat is not applicable for the definition of CDR1, as this annotation is not including the particular Lysine residue. In a particular embodiment, the CDR1 comprises or is the amino acid sequence of SEQ ID NO:1; CDR2 comprises or is the amino acid sequence of SEQ ID NO:2; and CDR3 comprises or is the amino acid sequence of SEQ ID NO:3. Said latter CDR regions being determined according to the MacCallum et al. (1996) definition (see also FIG. 1). Said CDRs, for instance as provided by SEQ ID NO:1, 2, and 3 as defined in MacCallum et al., and in particular the contribution of CDR1, provide the unique feature of the high affinity for rat serum albumin.

```
SEQ ID NO: 1 depicts the amino acid sequence of
CDR1 region of SA1_S30K (wherein the CDRs were
annotated according to MacCallum et al., 1996)
SEQ ID NO: 1: CDR1 SA1_S30K
KEYVMG SEQ ID NO: 2 depicts the amino acid sequence of
CDR2 region of SA1_S30K (wherein the CDRs
annotated according to MacCallum et al., 1996)
SEQ ID NO: 2: CDR SA1_S30K
FVAAISWSAGNIY SEQ ID NO: 3 depicts the amino acid sequence of
CDR3 region of SA1_S30K (wherein the CDRs
annotated according to MacCallum et al., 1996)
SEQ ID NO: 3: CDR3 SA1_S30K
AAGRYSAWYVAAYEYD
```

For numbering of the amino acid residues of an IVD different numbering schemes can be applied. For example, numbering can be performed according to the Kabat numbering system as applied to VHH domains from camelids in the article of Riechmann, L. and Muyldermans, S., 231(1-2), J Immunol Methods. 1999, also see FIG. 1, and used throughout this application (unless stated otherwise). Alternative methods for numbering the amino acid residues of VH domains, which can also be applied in an analogous manner to VHH domains, are known in the art. The delineation of the FR and CDR sequences can also be done by using the Kabat numbering, but other methods are applied as well in the art, such as the designation based on contact analysis and binding site topography as described in MacCallum et al., J. Mol. Biol. (1996) 262, 732-745, which was also followed in the present description, sequence annotation and claims of the invention (FIG. 1, and SEQ ID NO:1-3, and SEQ ID NO:4 for SA1_S30K VHH). The annotation of CDRs according to AbM (AbM is Oxford Molecular Ltd.'s antibody modelling package as described on http://www.bioinf.org.uk/abs/index.html), Chothia (Chothia and Lesk, 1987), Kabat (Kabat et al., 1991), and IMGT (LeFranc, 2014) differ slightly, and are for information provided as well in FIG. 1. It should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

In one embodiment, the polypeptide described herein comprises a serum albumin binding IVD comprising said CDRs as described herein, and further comprising an amino acid sequence in its FR3 region that corresponds to the FR3 region amino acid sequence of SEQ ID NO:4 (SA1_S30K), as depicted in SEQ ID NO:18 in view of the MacCallum CDR annotation. In another embodiment, the polypeptides described herein comprises the FR3 region corresponding to a humanized variant of SEQ ID NO:4 wherein said FR3 region has the amino acid sequence (according to Kabat numbering) wherein at position 73 and 74 any amino acid may be present, and/or wherein at position 78 a Valine or Leucine is present, and/or wherein at amino acid position 79 a histidine or Tyrosine is present, and/or wherein at position 82b a Threonine or Serine is present.

```
SEQ ID NO: 18 depicts the amino acid sequence of
FR3 from SA1_S30K (wherein the CDRs are
annotated according to MacCallum et al., 1996),
and corresponding to residues 60-96 of
SEQ ID NO: 4.
SEQ ID NO: 18: FR3 SA1_S30K
YADSVKGRFTISRDXXKNTVHLQMNTLRPEDTAVYYC
```

In one embodiment, XX is NA (for FR3 corresponding to SA1_S30K), and in other embodiments, XX is NS (for FR3 corresponding to SA1_S30K_h1-7), and in other embodiments, XX is any amino acid (further humanization variants of SA1_S30K).

In another embodiment, said polypeptide comprises an IVD which comprises the amino acid sequence of SEQ ID NO:4, or SA1_S30K VHH.

In another embodiment, said polypeptide comprising an IVD according to the invention, which comprises the amino acid sequence of a humanized variant of SEQ ID NO:4, or of SA1_S30K. To obtain said humanized variants of the invention, the skilled person analyzed the closest human homologue sequence from human, VH3-23 (GenBank: P01764.2)/J5, as depicted in SEQ ID NO:7, to substitute amino acid residues in the FR regions of SA1_S30K to more human-like sequences, often without affecting typical 'hallmark' VHH residues or CDR regions.

```
SEQ ID NO: 7 depicts the amino acid sequence of
the full length VH3-23/J5 human VHH (Uniprot
P01764.2)
SEQ ID NO: 7: VH3-23/J5
EVQLVESGGGLVQPGGSLRLSCAASGFTFSSYAMSWVRQAPGKGLEWVSA

ISSNGGSTYYADSVKGRFTISRDNSKNTLYLQMNSLRAEDTAVYYCARWG

QGTLVTVSS
```

Non-limiting examples are provided in Example 8 of the current application, and depicted in SEQ ID NOs: 8-11 (presented as h1-h4 in FIG. 5). Additional alternative examples or provided in FIG. 5 (as 'alternative h'), and also further in SEQ ID NOs: 15-17.

SEQ ID NO: 8 depicts the amino acid sequence of
the full length SA1_S30K humanized variant 1 VHH
SEQ ID NO: 8: SA1_S30K_human1
EVQLQESGGGLVQPGGSLRLSCAASGRNIKEYVMGWFRQAPGKEREFVAA

ISWSAGNIYYADSVKGRFTISRDNSKNTVHLQMNTLRPEDTAVYYCAAGR

YSAWYVAAYEYDYWGQGTLVTVSS

SEQ ID NO: 9 depicts the amino acid sequence of
the full length SA1_S30K humanized variant 2 VHH
SEQ ID NO: 9: SA1_S30K_human2
EVQLQESGGGLVQPGGSLRLSCAASGRNIKEYVMGWFRQAPGKEREFVAA

ISWSAGNIYYADSVKGRFTISRDNSKNTVYLQMNTLRPEDTAVYYCAAGR

YSAWYVAAYEYDYWGQGTLVTVSS

SEQ ID NO: 10 depicts the amino acid sequence of
the full length SA1_S30K humanized variant 3 VHH
SEQ ID NO: 10: SA1_S30K_human3
EVQLQESGGGLVQPGGSLRLSCAASGRNIKEYVMGWFRQAPGKEREFVAA

ISWSAGNIYYADSVKGRFTISRDNSKNTVHLQMNSLRPEDTAVYYCAAGR

YSAWYVAAYEYDYWGQGTLVTVSS

SEQ ID NO: 11 depicts the amino acid sequence of
the full length SA1_S30K humanized variant 4 VHH
SEQ ID NO: 11: SA1_S30K_human4
EVQLQESGGGLVQPGGSLRLSCAASGRNIKEYVMGWFRQAPGKEREFVAA

ISWSAGNIYYADSVKGRFTISRDNSKNTVYLQMNSLRPEDTAVYYCAAGR

YSAWYVAAYEYDYWGQGTLVTVSS

SEQ ID NO: 15 depicts the amino acid sequence of
the full length SA1_S30K humanized variant 5 VHH
SEQ ID NO: 15: SA1_S30K_human5
QVQLQESGGGLVQAGGSLRLSCAASGRNIKEYVMGWFRQAPGKEREFVAA

ISWSAGNIYYADSVKGRFTISRDNAKNTVYLQMNTLRPEDTAVYYCAAGR

YSAWYVAAYEYDYWGQGTQVTVSS

SEQ ID NO: 16 depicts the amino acid sequence of
the full length SA1_S30K humanized variant 6 VHH
SEQ ID NO: 16: SA1_S30K_human6
QVQLQESGGGLVQAGGSLRLSCAASGRNIKEYVMGWFRQAPGKEREFVAA

ISWSAGNIYYADSVKGRFTISRDNAKNTVHLQMNSLRPEDTAVYYCAAGR

YSAWYVAAYEYDYWGQGTQVTVSS

SEQ ID NO: 17 depicts the amino acid sequence of
the full length SA1_S30K humanized variant 7 VHH
SEQ ID NO: 17: SA1_S30K_human7
QVQLQESGGGLVQAGGSLRLSCAASGRNIKEYVMGWFRQAPGKEREFVAA

ISWSAGNIYYADSVKGRFTISRDNAKNTVYLQMNSLRPEDTAVYYCAAGR

YSAWYVAAYEYDYWGQGTQVTVSS

The humanized sequence variants should retain the favourable properties of the original VHH, which include antigen binding affinity, and biochemical and biophysical properties. When analysing humanized variants h1, h2, h3 and h4 (see Examples 8-10), a surprising observation concerned the clear increase in melting temperature, a measure of thermostability, which could be unambiguously linked to the substitution of amino acids at position 79, from H to Y, and at position 82b, from T to S. Each substitution contributed to an increase of 4° C. in melting temperature (h2 and h3), and a collaborative effect of an increase to 8° C. as compared to the SA1_S30K was observed in the h4 variant, which contained both substitutions. Even though those positions in known VHHs display those amino acids Y and S, respectively, it is considered here that in combination with the specific CDRs, an improved stability of serum albumin binding polypeptides has been defined. So, one embodiment relates to the polypeptide wherein said FR3 region has Y at position 79, and/or has S at position 82b.

It should be noted that the immunoglobulin single variable domains, in particular the Nanobody®, of the invention in their broadest sense are not limited to a specific biological source or to a specific method of preparation. For example, the immunoglobulin single variable domains of the invention, in particular the Nanobody®, can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "mutation" of a naturally occurring VHH domain to reduce binding to pre-existing antibodies, or by expression of a nucleic acid encoding such a mutated VHH domain; (5) by "cannelization" of a naturally occurring VH domain from any animal species, and in particular from a mammalian species, such as from a human being, or by expression of a nucleic acid encoding such a camelized VH domain; (6) by "cannelization" of a "domain antibody" or "Dab" as described in the art, or by expression of a nucleic acid encoding such a camelized VH domain; (7) by using synthetic or semi-synthetic techniques for preparing proteins, polypeptides or other amino acid sequences known per se; (8) by preparing a nucleic acid encoding a Nanobody® using techniques for nucleic acid synthesis known per se, followed by expression of the nucleic acid thus obtained; and/or (9) by any combination of one or more of the foregoing.

Again, it should be noted that humanized immunoglobulin single variable domains of the invention can be obtained in any suitable manner known per se (i.e. as indicated under points (1)-(9) above) and thus are not strictly limited to polypeptides that have been obtained using a polypeptide that comprises a naturally occurring VHH domain as a starting material.

Humanized immunoglobulin single variable domains, in particular Nanobody®, may have several advantages, such as a reduced immunogenicity, compared to the corresponding naturally occurring VHH domains. By humanized is meant mutated so that immunogenicity upon administration in human patients is minor or nonexistent. Such humanization generally involves replacing one or more amino acid residues in the sequence of a naturally occurring VHH with the amino acid residues that occur at the same position in a human VH domain, such as a human VH3 domain. Humanizing a single domain antibody, according to the present invention, comprises a step of replacing one or more of amino acids by their human counterpart as found for instance in the human consensus sequence, without that polypeptide losing its typical character, i.e. the humanization does not significantly affect the antigen binding capacity of the resulting polypeptide. The humanizing substitutions should be chosen such that the resulting humanized polypeptides still retain the favourable properties as defined herein. The skilled person will be able to select humanizing substitutions or suitable combinations of humanizing substitutions which optimize or achieve a desired or suitable balance between the favourable properties provided by the humanizing substitutions on the one hand and the favourable properties of naturally occurring VHH domains on the other hand.

Such methods are known by the skilled addressee. A human consensus sequence can be used as target sequence for humanization, but also other means are known in the art.

One alternative includes a method wherein the skilled person aligns a number of human germline alleles, such as for instance but not limited to the alignment of the IGHV3 alleles shown in FIG. 6, to use said alignment for identification of residues suitable for humanization in the target sequence. Also a subset of human germline alleles most homologous to the target sequence may be aligned as starting point to identify suitable humanisation residues. Alternatively, the VHH is analyzed to identify its closest homologue in the human alleles (as in Example 8), and used for humanisation construct design. A humanisation technique applied to Camelidae VHHs may also be performed by a method comprising the replacement of specific amino acids, either alone or in combination. Said replacements may be selected based on what is known from literature, are from known humanization efforts, as well as from human consensus sequences compared to the natural VHH sequences, or the human alleles most similar to the VHH sequence of interest. As can be seen from the data on the $V_{HH}$ entropy and $V_{HH}$ variability given in Tables A-5-A-8 of WO 08/020079, some amino acid residues in the framework regions are more conserved between human and Camelidae than others. Generally, although the invention in its broadest sense is not limited thereto, any substitutions, deletions or insertions are preferably made at positions that are less conserved. Also, generally, amino acid substitutions are preferred over amino acid deletions or insertions. For instance, a human-like class of Camelidae single domain antibodies contain the hydrophobic FR2 residues typically found in conventional antibodies of human origin or from other species, but compensating this loss in hydrophilicity by other substitutions at position 103 that substitutes the conserved tryptophan residue present in VH from double-chain antibodies. As such, peptides belonging to these two classes show a high amino acid sequence homology to human VH framework regions and said peptides might be administered to a human directly without expectation of an unwanted immune response therefrom, and without the burden of further humanisation. Indeed, some Camelidae VHH sequences display a high sequence homology to human VH framework regions and therefore said VHH might be administered to patients directly without expectation of an immune response therefrom, and without the additional burden of humanization.

Other VHH sequences in fact require humanization techniques to typically lead to a variant with favorable conditions to react with the target protein when administered to a subject. The humanizing substitutions should be chosen such that the resulting humanized amino acid sequence and/or VHH still retains the favourable properties of the VHH as defined herein. A skilled person will generally be able to determine and select suitable humanizing substitutions or suitable combinations of humanizing substitutions, based on the disclosure herein and optionally after a limited degree of experimentation, which may for example involve introducing a limited number of possible humanizing substitutions and determining their influence on the properties of the VHH thus obtained. Generally, as a result of humanization, the amino acid sequence and/or VHH of the invention may become more "human-like", while still retaining the favorable properties of the VHH of the invention as described herein. As a result, such humanized amino acid sequence and/or VHH may have several advantages, such as a reduced immunogenicity, compared to the corresponding naturally occurring $V_{HH}$ domain. Suitable mutations, in particular substitutions, can be introduced during humanization to generate a polypeptide with reduced binding to pre-existing antibodies (reference is made for example to WO 2012/175741 and WO2015/173325), for example at at least one of the positions: 11, 13, 14, 15, 40, 41, 42, 82, 82a, 82b, 83, 84, 85, 87, 88, 89, 103, or 108.

The amino acid sequences and/or VHH of the invention may be suitably humanized at any framework residue(s), such as at one or more Hallmark residues (as defined herein) or at one or more other framework residues (i.e. non-Hallmark residues) or any suitable combination thereof. Depending on the host organism used to express the amino acid sequence, VHH or polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation.

In some cases, at least one of the typical Camelidae hallmark residues with hydrophilic characteristics at position 37, 44, 45 and/or 47 is replaced (see WO2008/020079 Table A-03). Another example of humanization includes substitution of residues in FR 1, such as position 1, 5, 11, 14, 16, and/or 28; in FR3, such as positions 73, 74, 75, 76, 78, 79, 82b, 83, 84, 93 and/or 94; and in FR4, such as position 103, 104, 108 and/or 111 (see WO2008/020079 Tables A-05-A08; all numbering according to the Kabat).

In one embodiment, the polypeptide described herein comprises a serum albumin binding IVD, comprising the amino acid sequence of a humanized variant of SEQ ID NO:4. Alternatively, the IVD comprises the amino acid sequence of SEQ ID NO:8-11 or SEQ ID NO:15-17, or a further humanized variant thereof. A humanization approach used to determine humanization variants of SEQ ID NO:4, or further humanization of SEQ ID NO:8-11 and 15-17, is alternatively based on the human consensus aligned with human germline alleles as depicted in FIG. 6. Different methods are suitable to derive which amino acid residues are suitable for substitution. Based on the human sequences provided for in the alignment of FIG. 6, the following positions (according to Kabat numbering) are potentially substituted for humanizing the VHH of the invention: in FR1 position 1 (E, Q); position 5 (V or L), position 11 (L or V), position 13 (Q, K, R), position 14 (P), position 16 (G, R) and position 29 (I, F, V); in FR2 position 37 (F, V, I, A); in FR3 position 59 (Y, G, N, D, E, H), position 61 (D, A, G), position 62 (S, P), position 73 (N, D); position 74 (A, S), position 77 (T, S), position 83 (R, K), position 84 (A, T), position 87 (T, M), position 89 (V, L); in FR4 position 108 (Q, L). When the serum albumin binding IVD of the invention is positioned at the N-terminus in a therapeutic application (therapeutic agent or multispecific construct), the N-terminus should contain a D at position 1 (for instance an E1D mutation compared to SEQ ID NO:8, 9, 10 or 11).

FIG. 5 provides an alignment of SA1_S30K VHH with a number of humanized versions of SA1_S30K VHH (h1-4; depicted in SEQ ID NOs: 8-11) also exemplified in Examples 8-10, or alternative options for humanization of SA1_S30K (alternative h in FIG. 5). The main differences between SA1_S30K and the humanized versions are: position 1: Q to E/D; position 5: Q to V; position 14: A to P; position 73: N to any amino acid (X), or position 74: A to S or any amino acid; position 78: V to L; position 79: H to Y; position 82b: T to S; and/or position 108: Q to L.

Also within the scope of the invention are natural or synthetic analogs, mutants, variants, alleles, parts or fragments (herein collectively referred to as "variants") of the immunoglobulin variable domain (IVD) or immunoglobulin single variable domains (ISVD), in particular the VHH or the Nanobody®, of the invention as defined herein, and in particular variants of the VHH of SEQ ID NO:4 or of the humanized VHH variant of SEQ ID NO:4. Thus, according to one embodiment of the invention, the term "immunoglobulin variable domain of the invention" or "VHH of the invention" in its broadest sense also covers such variants. Generally, in such variants, one or more amino acid residues may have been replaced, deleted and/or added, compared to the immunoglobulin single variable domains of the invention as defined herein. Such substitutions, insertions or deletions may be made in one or more of the FR's and/or in one or more of the CDRs (SEQ ID NOs:1-3), and in particular variants of the FRs and CDRs of the immunoglobulin variable domains of SEQ ID NO:4. Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence, as can be measured electronically by making use of algorithms such as PILEUP and BLAST. Software for performing BLAST analyses is publicly available through the National Center for Biotechnology Information (http://www/ncbi.nlm.nih.gov/). It will be understood that for determining the degree of amino acid identity of the amino acid sequences of the CDRs of one or more sequences of the immunoglobulin variable domains, the amino acid residues that form the framework regions are disregarded. Similarly, for determining the degree of amino acid identity of the amino acid sequences of the FR's of one or more sequences of the immunoglobulin single variable domains of the invention, the amino acid residues that form the complementarity regions are disregarded. Such variants of immunoglobulin variable domains may be of particular advantage since they may have improved potency/affinity. By means of non-limiting examples, a substitution may for example be a conservative substitution and/or an amino acid residue may be replaced by another amino acid residue that naturally occurs at the same position in another VHH domain. Thus, any one or more substitutions, deletions or insertions, or any combination thereof, that either improve the properties of the immunoglobulin variable domains of the invention or that at least do not detract too much from the desired properties or from the balance or combination of desired properties of the Nanobody® of the invention (i.e. to the extent that the immunoglobulin single variable domains is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the immunoglobulin variable domains thus obtained.

In a further embodiment, the polypeptide as described herein comprises the IVD as described herein, wherein said is an IVD conjugate. The term "conjugated to", as used herein, refers, in particular, to chemical and/or enzymatic conjugation resulting in a stable covalent link. An "IVD conjugate" or an "ISVD conjugate" is referred to herein as a polypeptide comprising an IVD or ISVD of the invention which is coupled (or conjugated or connected, which are equivalent terms in the art) with a specific moiety, herein further defined as the "conjugated moiety" or "conjugate". Coupling to obtain the IVD conjugate or ISVD conjugate can occur via a specific amino acid (e.g. lysine, cysteine) present in the IVD or ISVD. As used herein, the term "conjugated moiety", or "conjugate", comprises agents (e.g. proteins (e.g. a second IVD or ISVD), nucleotide sequences, lipids, (other) carbohydrates, peptides, drug moieties (e.g. cytotoxic drugs, antibody drug-conjugates or payload), tracers and detection agents) with a particular biological or specific functional activity. For example, an IVD or ISVD conjugate comprising a polypeptide according to the invention and a conjugated moiety has at least one additional function or property as compared to the unconjugated IVD or ISVD polypeptide of the invention. For example, an IVD or ISVD conjugate comprising a polypeptide of the invention and a cytotoxic drug being the conjugated moiety results in the formation of a binding polypeptide with drug cytotoxicity as second function (i.e. in addition to antigen binding conferred by the IVD or ISVD polypeptide, in particular cases serum albumin binding). In yet another example, the conjugation of a second binding polypeptide to the IVD or ISVD polypeptide, such as a therapeutic moiety, of the invention may confer additional binding properties. In certain embodiments, where the conjugated moiety is a genetically encoded therapeutic or diagnostic protein or nucleotide sequence, the conjugated moiety may be synthesized or expressed by either peptide synthesis or recombinant DNA methods that are well known in the art. In another aspect, where the conjugated moiety is a non-genetically encoded peptide, e.g. a drug moiety, the conjugated moiety may be synthesized artificially or purified from a natural source.

In a particular embodiment, the conjugation involves the lysine of CDR1, or the first lysine residue of SEQ ID NO:1, or alternatively, the lysine present at position 30 of SEQ ID NO:4. Conjugation may be performed by any method described in the art and some non-limiting illustrative embodiments will be outlined in the example section. In certain embodiments the conjugated moiety comprises various therapeutic agents including i.e. anti-inflammatory, anti-cancer, cytotoxic, anti-infective (e.g., anti-fungal, antibacterial, anti-parasitic, anti-viral, etc.), and anesthetic therapeutic agents. In specific embodiments the conjugated moiety is an enzyme capable of converting a prodrug which is converted into a toxic drug. A toxic agent (e.g. a toxin, a cytotoxic drug, a radionuclide) can also be suitable for therapeutic purposes and is particularly useful in cancer therapy.

In a particular embodiment of the invention, said IVD is conjugated to a drug or payload. As a proof of principle, the invention provides a conjugation to biotin in one specific embodiment. Such biotinylated IVD conjugates were analysed for serum albumin binding affinity, confirming that conjugation of said payload to a lysine residue in the CDR1 region did not affect its binding affinity. In addition, coupling a larger payload (e.g. horse radish peroxidase as a marker protein) would reveal further proof of principle that the lysine in the SA1_S30K on position 30 is suitable as a payload conjugation site while retaining the function of serum albumin binding or half-life extension in human and rodents, such as rats and mice.

A further specific example of an IVD-conjugate is an antibody-drug-conjugate (ADC). In principal, every agent suitable for therapeutic purposes is envisaged herein. Therapeutic agents as described are typically small molecules or biologics, but therapeutic agents can also be of another origin what should be clear to the skilled person and the invention should not be limited thereto. Those ADC drugs are currently an active area of research, focused primarily on oncology therapeutics, but also to a limited extent on other areas such as infectious disease (Bessire et al., 2016) are generally composed of three major components: an antibody (or IVD) for the selective targeting of tumor cell surface antigens, a cytotoxic payload, and a linker unit which connects these two moieties, which in this case also constitutes a serum albumin binding IVD. The ADCs are internalized by endocytosis upon binding to cell surface antigens, and are subsequently trafficked to the endosomes and/or lysosomes. In these compartments, the cytotoxic payload moiety is released either through antibody catabolism or through cleavage of the linker via proteases, pH-triggered hydrolysis, or disulfide reduction. For ADCs with a cleavable linker, the cleavage trigger is usually determined by the nature of the linker used. For example, the commonly used cleavable linker valine-citrulline p-aminobenzyl carbamate (vc-PABC) is a substrate for the intracellular cysteine protease cathepsin B. Cleavable-linker ADCs typically release the unmodified payload as the active moiety. Noncleavable linker ADCs, however, do not contain a mechanism of rapid chemical or enzymatic release, but instead rely on the degradation of the antibody for release of the active species. These ADCs may contain any of a host of chemical linkers, or no linker at all, and typically release the cytotoxic payload with the linker and one or more amino acids from the antibody or IVD.

In certain embodiments the IVD-conjugates comprise a linker between the lysine and the conjugate, or conjugate moiety. Certain linkers are more useful than others and the use of a specific linker will depend on the application. In general various linkers known in the art can be used to link the IVD and the conjugated moiety according to the invention. As should be clear, cleavable and non-cleavable linkers can be employed to achieve the desired release profile. In general, the optimal combination of linker and conjugation chemistry must be uniquely tailored to correlate each unique facet: the IVD, the conjugated moiety, and the profile of the disease to be treated. For reviews on antibody-drug conjugates and linkers used herein see for example McCombs and Owen (2015) and Lu, et al., (2016) as well as a recent review by Pillow (2017) describing a novel quaternary ammonium salt linker useful in conjugates for the treatment of cancer and infectious diseases. Still other suitable spacers or linkers will be clear to the skilled person, and may generally be any linker or spacer used in the art. In specific aspects the linkers or spacers are suitable for use in applications which are intended for pharmaceutical use. For example, a linker between the lysine and the conjugate may in certain aspects also be a suitable amino acid sequence, and in particular amino acid sequences of between 1 and 50, or more specifically, between 1 and 30 amino acid residues. Some examples of such amino acid sequences include Gly-Ser (GS) linkers. Still other suitable linkers generally comprise organic compounds or polymers, in particular those suitable for use in polypeptides for pharmaceutical use. For instance, poly(ethyleneglycol) moieties have been used to link antibody domains, see for example WO 04/081026. It is encompassed within the scope of the invention that the length, the degree of flexibility and/or other properties of the linker may have some influence on the properties of the final IVD conjugate of the invention, including but not limited to the affinity, specificity or avidity for a specific target. Based on the disclosure herein, the skilled person will be able to determine the optimal linker for use in a specific IVD of the invention, optionally after some limited routine experiments. For example, in multivalent or multispecific IVDs of the invention that comprise building blocks, directed against a first and second target, the length and flexibility of the linker is preferably such that it allows each building block to bind to its cognate target. Again, based on the disclosure herein, the skilled person will be able to determine the optimal linker for use in a specific IVD of the invention, optionally after some limited routine experiments. Finally, when two or more linkers are used in the IVD of the invention, these linkers may be the same or different. Again, based on the disclosure herein, the skilled person will be able to determine the optimal linkers for use in a specific polypeptide of the invention, optionally after some limited routine experiments.

In yet another embodiment, the invention provides methods to produce an IVD conjugate of the invention. Generally, such methods start by introducing an expression vector comprising a nucleotide sequence encoding an IVD according to the invention in a suitable cell of choice, followed by expressing the IVD polypeptide for some time, purifying the IVD polypeptide and linking of a specific conjugated moiety to the purified IVD polypeptide. The coupling method itself is generally carried out in vitro. Several possibilities exist in the art to link a specific conjugated moiety an IVD polypeptide of the invention. Generally spoken there are chemical, enzymatic and combined chemo-enzymatic conjugation strategies to carry the coupling reaction. In a particular embodiment, a polypeptide comprising an IVD-conjugate of the invention is used to modulate the circulation half-life or to increase the IVD stability, for selective targeting, to modulate immunogenicity of the IVD-conjugate or for detection purposes. In yet another embodiment the IVD-conjugates of the invention are used as a medicament.

In fact, a further aspect of the invention relates to said polypeptides of the invention comprising a serum albumin binding IVD, for use to increase the half-life of a therapeutic moiety.

Currently, half-life extension of biotherapeutics is dominated by strategies utilizing albumin binding or fusion, fusion to an immunoglobulin Fc region and PEGylation (Konterman, 2016). Hence, the use of the serum albumin binding polypeptides of the current invention for half-life extension or increased half-life for a therapeutic moiety or biologicals is certainly a very auspicious application of said invention. In fact, the therapeutic moiety of the invention is provided by linking or coupling the serum albumin binding polypeptide to said therapeutic moiety, which can basically be any type of molecule, and preferably is a protein, or more particularly comprises an IVD. Said coupling or linking may be via the lysine in CDR1, but may as well be via other residues, such as the N- or C-terminus of the IVD or polypeptide of the invention.

One embodiment further relates to a therapeutic agent with increased serum half-life, characterized in that said agent (which may be a larger polypeptide or a macromolecule) comprises the polypeptide comprising the IVD of the invention, and in addition a therapeutic moiety. Said therapeutic agent is characterized in that is has a longer half-life as compared to the same therapeutic agent lacking the serum albumin binding polypeptide of the invention.

The polypeptide of the invention comprising an IVD binding to serum albumin according to the current invention, or the therapeutic agent of the invention is in various embodiments also applied for use as a medicament.

In specific embodiments, said use as a medicament will be related to the presence of a therapeutic moiety within said polypeptide, besides the IVD comprising serum albumin binding affinity. In said embodiments, the invention alternatively provides a multispecific construct.

More specifically, said multispecific construct comprises said polypeptide with a serum albumin binding IVD according to the present invention, and at least one therapeutic moiety. Hence, said multispecific or multivalent constructs or polypeptides comprise at least one antigen binding site, with affinity for serum albumin, and at least one more therapeutically useful moiety, which in certain embodiments also comprises an antigen-binding site to target the therapeutically relevant protein. In embodiments wherein said therapeutic moiety comprise an IVD, the invention comprises fused variable domains, such as multivalent and/or multispecific constructs. For multivalent and multispecific polypeptides containing one or more $V_{HH}$ domains and their preparation, reference is also made to Conrath et al. (2001) as well as to for example WO 96/34103 and WO 99/23221. Alternatively, embodiments relate to multispecific or multivalent constructs wherein said therapeutic moiety comprises a fragment of an IVD, or an ISVD. Finally, various embodiments relate to multispecific or multivalent constructs according to the current invention, wherein the polypeptide is linked to the at least one therapeutic moiety via a linker or spacer.

In another aspect of the invention, a nucleotide sequence or nucleic acid or nucleic acid molecule is provided, encoding the polypeptides of the present invention or the multispecific constructs of the present invention.

An alternative embodiment relates to a vector comprising said nucleotide sequence. The term "vector", as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Typically, an "expression vector" comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to. The term "operatively" or "operably" "linked" as used herein refers to a functional linkage between the expressible promoter sequence and the DNA region or gene of interest, such that the promoter sequence is able to initiate transcription of the gene of interest, and refers to a functional linkage between the gene of interest and the transcription terminating sequence to assure adequate termination of transcription in eukaryotic cells. Cloning vectors are generally used to engineer and amplify a certain desired DNA fragment and may lack functional sequences needed for expression of the desired DNA fragments.

Another embodiment relates to a host cell or expression host comprising the polypeptide, or the multispecific construct, or the nucleic acid sequence or molecule provided by the present invention. The term "host cell", "expression host", or "host" refers to the cellular system used to express the protein or nucleic acid of interest, in a recombinant manner. A host cell can relate to a "higher eukaryotic cell" referring to eukaryotic cells that are not cells from unicellular organisms. In other words, a higher eukaryotic cell is a cell from (or derived from, in case of cell cultures) a multicellular eukaryote such as a human cell line or another mammalian cell line (e.g. a CHO cell line). Typically, the higher eukaryotic cells will not be fungal cells. Particularly, the term generally refers to mammalian cells, human cell lines and insect cell lines. More particularly, the term refers to vertebrate cells, even more particularly to mammalian cells or human cells. The higher eukaryotic cells as described herein will typically be part of a cell culture (e.g. a cell line, such as a HEK or CHO cell line), although this is not always strictly required (e.g. in case of plant cells, the plant itself can be used to produce a recombinant protein). A host cell can also relate to a "lower eukaryotic cell" as used herein where a filamentous fungus cell or a yeast cell is meant. Yeast cells can be from the species *Saccharomyces* (e.g. *Saccharomyces cerevisiae*), *Hansenula* (e.g. *Hansenula polymorpha*), *Arxula* (e.g. *Arxula adeninivorans*), *Yarrowia* (e.g. *Yarrowia lipolytica*), *Kluyveromyces* (e.g. *Kluyveromyces lactis*), or *Komagataella phaffii* (Kurtzman, 2009), which was previously named and better known under the old nomenclature as *Pichia pastoris* and also further used herein. According to a specific embodiment, the lower eukaryotic cells are *Pichia* cells, and in a most particular embodiment *Pichia pastoris* cells. In specific embodiments the filamentous fungus cell is *Myceliopthora thermophila* (also known as C1 by the company Dyadic), *Aspergillus* species (e.g. *Aspergillus nidulans, Aspergillus niger, Aspergillus oryzae, Aspergillus japonicus*), *Fusarium* species (e.g. *Fusarium venenatum*), *Hypocrea* and *Trichoderma* species (e.g. *Trichoderma reesei*). Host cells relating to "prokaryotic cells" typically refer to non-pathogenic prokaryotes like bacterial cells such as for example *E. coli, Lactococcus* and *Bacillus* species.

Another aspect of the invention relates to a pharmaceutical composition comprising at least one protein comprising an IVD with serum albumin binding properties according to the invention, or at least one therapeutic agent of the invention, or at least one multispecific construct of the invention, and optionally at least one pharmaceutically acceptable carrier, diluent or excipient.

The present invention hence includes pharmaceutical compositions that are comprised of a pharmaceutically acceptable carrier, diluent or excipient, and a pharmaceutically effective amount of polypeptides, comprising an IVD, or an IVD-conjugate, binding to serum albumin, and optionally, also conjugated to another therapeutic or diagnostic moiety, in a multispecific construct, or conjugated to a drug, via its lysine in CDR1. A "carrier", or "adjuvant", in particular a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. Preferably, a pharmaceutically acceptable carrier or adjuvant enhances the immune response elicited by an antigen. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, stabilizing agents, flavouring agents or colorants. A "diluent", in particular a "pharmaceutically acceptable vehicle", includes vehicles such as water, saline, physiological salt solutions, glycerol, ethanol, etc. Auxiliary substances such as wetting or emulsifying agents, pH buffering substances, preservatives may be included in such vehicles.

A pharmaceutically effective amount of polypeptides, or conjugates of the invention and a pharmaceutically acceptable carrier is preferably that amount which produces a result or exerts an influence on the particular condition being treated. In general, "therapeutically effective amount", "therapeutically effective dose" and "effective amount" means the amount needed to achieve the desired result or results. One of ordinary skill in the art will recognize that the potency and, therefore, an "effective amount" can vary for the polypeptide binding serum albumin, and/or other antigens via other therapeutic moieties present in the polypeptide of the invention. One skilled in the art can readily assess the potency of the antibody.

The polypeptides, and conjugates of the invention and a pharmaceutically acceptable carrier can be administered with pharmaceutically acceptable carriers well known in the art using any effective conventional dosage form, including immediate, slow and timed release preparations, and can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmically, intrathecally, intracerebroventricularly, sublingually, rectally, vaginally, and the like. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be taken into account by the clinician. The pharmaceutical composition of this invention can be lyophilized for storage and reconstituted in a suitable carrier prior to use. When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN™, PLURONICS™ or PEG and the like. The preparation containing pharmaceutical composition of this invention should be sterilized before injection. This procedure can be done using sterile filtration membranes before or after lyophilization and reconstitution. The pharmaceutical composition is usually filled in a container with sterile access port, such as an i.v. solution bottle with a cork.

A further aspect of the invention relates to a method to produce a serum albumin binding polypeptide comprising the steps of
i. Expression of the polypeptide, the multispecific construct, or the nucleotide sequence or nucleic acid encoding said polypeptide or multispecific construct according to the present invention, in a suitable expression system or host cell, and
ii. Purification or isolation of said serum albumin binding polypeptide.

With purification or isolation of said expressed polypeptide is for instance meant, without limitation, affinity-based purification such as affinity chromatography, affinity purification, immunoprecipitation, protein detection, immunochemistry, surface-display, amongst others, and all well-known in the art.

In another embodiment, the invention provides a method to prolong the half-life of a therapeutic agent in a subject, comprising administering a pharmaceutical composition according to the invention.

Yet another aspect of the invention relates to a kit comprising a polypeptide, multispecific construct or nucleic acid according to the invention. The kit may further comprise a combination of reagents such as buffers, molecular tags, vector constructs, reference sample material, as well as a suitable solid supports, cells, nucleic acids, and the like. Such a kit may be useful for any of the applications of the present invention as described herein.

Also encompassed within the scope of the present invention is a solid support or resin comprising a polypeptide comprising an IVD with serum albumin binding affinity according to the present invention. Non-limiting examples of suitable solid supports include beads, columns, slides, chips or plates. More specifically, the solid supports may be particulate (e. g. beads or granules, generally used in extraction columns) or in sheet form (e. g. membranes or filters, glass or plastic slides, microtiter assay plates, dipstick, capillary fill devices or such like) which can be flat, pleated, or hollow fibers or tubes. The following matrices are given as examples and are not exhaustive, such examples could include silica (porous amorphous silica), i. e. the FLASH series of cartridges containing 60A irregular silica (32-63 um or 35-70 um) supplied by Biotage (a division of Dyax Corp.), agarose or polyacrylamide supports, for example the Sepharose range of products supplied by Amersham Pharmacia Biotech, or the Affi-Gel supports supplied by Bio-ad. In addition, there are macroporous polymers, such as the pressure-stable Affi-Prep supports as supplied by Bio-Rad. Other supports that could be utilised include; dextran, collagen, polystyrene, methacrylate, calcium alginate, controlled pore glass, aluminium, titanium and porous ceramics. Alternatively, the solid surface may comprise part of a mass dependent sensor, for example, a surface plasmon resonance detector. Further examples of commercially available supports are discussed in, for example, Protein Immobilisation, R. F. Taylor ed., Marcel Dekker, Inc., New York, (1991). Immobilization may be either non-covalent or covalent, using techniques known in the art.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1: Generation of Non-Glycosylated Variant of the Serum Albumin Binding VHH SA1 and Off-Rate Determination The human albumin binding VHH SA1 (WO2014/037419; present application SEQ ID NO: 5) contains a putative N-glycosylation site at position 28 based on the presence of the NIS glycosylation consensus sequence at positions 28-30. The site was shown to be prone to partial glycosylation when SA1 was expressed in *Pichia pastoris*. Hence an SA1 mutant variant without glycosylation consensus sequence was designed by mutating the serine at position 30 to a lysine amino acid, SA1_S30K (SEQ ID NO: 4).

This SA1 mutant variant SA1_S30K, as well as a benchmark VHH also binding serum albumin (ALBS; SEQ ID NO:62 from EP1888641B1) and its non-mutated form SA1 were sub-cloned into the pHEN6c expression vector (Ghahroudi et al., 1997) between a pelB leader signal sequence (for VHH periplasmic transport) and a C-terminal hexa-histidine (His6) tag. The vectors were electro-transformed into *E. coli* WK6 and inoculated onto LB-agar ampicillin plates. Clones were seeded in 1 mL of TB+ampicillin medium. After 5 h, VHH production was induced with 1 mM of IPTG. After overnight production, the cell cultures were centrifuged and cells were resuspended in TES buffer (Tris pH8.0+sucrose and EDTA). After 2 h of incubation, water was added for another 4 h incubation. The bacteria were removed through centrifugation, after which the periplasmic extracts (PE) were immediately frozen at −80° C.

All PE's were analyzed for off-rate ranking at a ¼ dilution in a buffer at neutral pH (PBS) and a buffer at low pH (75 mM Na-acetate, pH 5.5) (Table 1). Off-rate was analyzed by BioLayer Interferometry on an Octet RED96 (Fortebio) instrument using human serum albumin (HSA) coated Octet AR2G sensors (HSA was coupled at 20 μg/mL at pH 5.0 as detailed in Fortebio Technical Note 26).

Based on the observed binding level at both pH conditions, the off-rate at both pH conditions and the biophysical properties of the amino acids, the SA1_S30K mutant variant was concluded to be suitable for further analysis.

TABLE 1

Off-rate screening results of SA1 S30K as compared to the controls

| | Run in PBS | | | Run in 75 mM NaAc buffer pH 5.5 | | | |
|---|---|---|---|---|---|---|---|
| | Response | | | Response | | | |
| Name | (nm) | $k_{dis}$ (1/s) | Dissoc $R^2$ | (nm) | $k_{dis}$ (1/s) | $k_{dis}$ Error | Dissoc $R^2$ |
| SA1_S30K | 0.250 | 1.41E−03 | 0.996 | 0.438 | 1.81E−03 | 1.26E−05 | 0.998 |
| SA1 | 0.025 | 1.99E−03 | 0.790 | 0.029 | 1.19E−03 | 3.36E−05 | 0.987 |
| SA1 | 0.029 | 2.22E−03 | 0.703 | 0.048 | 9.72E−04 | 1.94E−05 | 0.996 |
| Alb8 | 0.109 | 1.91E−03 | 0.996 | 0.550 | 2.88E−03 | 1.37E−05 | 0.998 |
| Alb8 | 0.279 | 3.34E−03 | 0.999 | 0.176 | 2.53E−03 | 0.000072 | 0.952 |

Response in nanometer (nm), off-rate ($k_{dis}$) per second (1/s), error on off-rate ($K_{dis}$ error) and determination coefficient (Dissoc $R^2$)

Example 2: Yield Upon Recombinant Expression and Purification of the SA1_S30K Mutant Variant VHH The SA1_S30K variant was expressed in 1 L of TB medium (3 bottles), and compared to the SA1 non-mutated VHH as well as the Alb8 benchmark. Small-scale overnight cultures were started in 5 mL of LB+ampicillin for each VHH. These were used to inoculate 3 shaker flasks with 330 mL TB+ampicillin/glucose. When the $OD_{600}$ of the cultures reached 0.8 the cultures were induced by adding 1 mM of IPTG (final concentration). The following day the cells were spun down and the pellets were weighed. Most cultures grew to $OD_{600}$ higher than 20 and had a clear supernatant after centrifugation.

The pellets were osmotically shocked by incubating them in 12 mL TES buffer for 3 h and then adding 18 mL water. After overnight incubation at 4° C., the PE's were collected by centrifugation. The pellets were then osmotically shocked again. When all extracts were collected, 1 mL of His-select matrix (Sigma-Aldrich) was added to each individual PE. The mixture was incubated for 1 h at 4° C. before being collected in an empty column. After reapplying the PE over the column a second time, the matrix was washed with PBS+20 mM imidazole. Finally, the VHHs were eluted by adding PBS+0.5M imidazole and collecting 1 mL fractions. These fractions obtained after this immobilized metal affinity chromatography (IMAC) were measured on nanodrop at 280 nm to gauge the amount of VHH collected. The fractions containing substantial amounts of protein were pooled and loaded onto a gel filtration (GF) column. All fractions from the VHH monomer peak were collected and pooled. The final VHH yields are listed in Table 2.

Remarkably, the SA1_S30K variant showed a higher yield as compared to the original SA1 VHH, and as compared to the benchmark Alb8.

TABLE 2

Yield after His-select and size exclusion chromatography of the SA1_S30K variant as compared to controls.

| Name | after IMAC (mg) | after GF (mg) |
|---|---|---|
| SA1_S30K | 53.4 | 39.2 |
| SA1 | 44.7 | 27.0 |
| Alb8 | 31.2 | 20.6 |

Example 3: Thermal Stability of the SA1_S30K Mutant Variant VHH

The thermostability of the VHH SA1_S30K mutant variant was determined to analyse whether the stability would be affected by the mutation in the purified VHH as compared to the SA1. Thermostability was determined at a protein concentration of 0.5 mg/mL, for Sypro Orange incorporation during 0.5° C. Sypro Orange incorporation was monitored in a Biorad Realtime PCR machine. The resulting values were fitted using a Boltzmann sigmoidal fit. Based on this fit the melting temperature (Tm) was determined for each VHH (Table 3). SA1_S30K showed a similar thermostability as compared to the non-mutated SA1, and showed a much higher thermostability compared to the benchmark.

TABLE 3

Tm of SA1_S30K variant as compared to controls.

| Name | Tm (° C.) |
|---|---|
| SA1_S30K | 76.99 |
| SA1 | 76.75 |
| Alb8 | 59.79 |

Example 4: Affinity of SA1_S30K Mutant Variant VHH for Serum Albumin

Affinity for human, cynomolgus monkey, mouse, rat, guinea pig, rabbit and bovine serum albumin was determined by BioLayer Interferometry (Octet RED96 instrument; Fortebio) for the SA1_S30K mutant variant as well as the original SA1 VHH and the benchmark Alb8. For this purpose, serum albumin of each species was coupled to AR2G sensors (Fortebio) as described in Example 1 for HSA.

Based on an initial profiling, a full kinetic profile was determined for the benchmark VHH Alb8, for SA1 and for the SA1_S30K variant from 100 nM serially diluted ½ down to 1.5 nM. However, due to the low affinity interaction to rabbit albumin, concentrations starting at 1600 nM were used down to 25 nM for this albumin. The resulting values for each VHH are presented in Table 4.

The affinity to human serum albumin is comparable for all tested VHHs. Bovine albumin did not show detectable binding affinity for any of the VHHs.

As compared to the benchmark, the cyno (Uniprot A2V924), mouse (Uniprot P07724, SEQ ID NO:13) and rat albumin (Uniprot P02770, SEQ ID NO:14) affinity was significantly higher for the SA1 and SA1_S30K VHHs. And surprisingly, the affinity for rat and mouse albumin was improved for the SA1_S30K mutant variant as compared to SA1.

In conclusion, the affinity ($K_D$) of SA1_S30K VHH (i.e. VHH depicted in SEQ ID NO:4) for rat albumin was shown to be 0.02 nM or 20 pM, which is much higher as compared to other VHHs, such as SA1 (20 times lower) or Alb8 (10,000 times lower). Less pronounced, but also higher is the affinity ($K_D$) of SA1_S30K VHH for mouse serum albumin, which is 0.29 nM or 290 pM, as compared to SA1 (2 times lower) or Alb8 (15 times lower).

Example 5: Biotinylation of SA1_S30K Mutant Variant VHH

The non-mutated control SA1 VHH and the SA1_S30K mutant variant VHH were labeled with biotin ("No Weigh" NHS-PEG4-Biotin kit from Thermo-Fisher) at a 5/1 molar ratio of biotin/VHH. Binding activity was initially assessed with ELISA and subsequently affinity determination was done by BioLayer Interferometry (OctetRED96 instrument; Fortebio).

1) ELISA: in brief HSA was coated (ON, 4° C., 5 μg/mL, carbonate buffer) after which plates were blocked with 1% casein (RT, 1 h). Subsequently a serial (0.5 log) dilution of biotinylated VHHs were incubated with a starting concentration of 3 μg/mL (2 h, RT, PBS—0.05% Tween 20-0.1% caseine). Finally, biotinylated VHH binding was detected with streptavidin-HRP (1 h, RT, PBS—0.05% Tween 20—0.1% caseine) and OPD substrate. Color reacting was stopped by adding 1 M $H_2SO_4$ and the OD read at 490 nm. Washing steps between incubations were done using PBS-0.05% Tween20.

2) Affinity: HSA was coated on octet AR2G tips as described in Example 1. Based on the previous data SA1 and SA1_S30K VHHs were used from 100 nM serially diluted ½ down to 1.5 nM.

The observed ELISA signal was clearly higher for the biotinylated SA1_S30K VHH variant (FIG. 2) which is likely related to the additional lysine residue at position 30. Although this lysine is part of CDR1 (SEQ ID NO:1; according to the CDR definition of MacCallum et al., Chothia, or AbM), this biotinylation did remarkably not affect the affinity of the biotinylated SA1_S30K VHH for HSA (Table 5: changes in $K_D$ or $k_{on}$ or $k_{off}$<2-fold).

TABLE 5

Affinity of (biotinylated) SA1_S30K and SA1 control for binding to HSA.

| Test item | $K_D$ (nM) | $k_{on}$ (s$^{-1}$.nM$^{-1}$) | $k_{off}$ (s$^{-1}$) |
|---|---|---|---|
| SA1 | 1.15E−09 | 1.92E+05 | 2.20E−04 |
| SA1-biotinylated | 1.97E−09 | 8.43E+04 | 1.66E−04 |

TABLE 4

Serum albumin affinity ($K_D$ in nM) of SA1_S30K variant as compared to the controls.

| Name | human $K_D$ | mouse $K_D$ | rat $K_D$ | cyno $K_D$ | rabbit $K_D$ | guinea pig $K_D$ | bovine $K_D$ |
|---|---|---|---|---|---|---|---|
| SA1_S30K | 0.91 | 0.29 | 0.02 | 0.38 | 1100 | NB | NB |
| SA1 | 0.90 | 0.66 | 0.45 | 0.37 | 600 | NB | NB |
| Alb8 | 0.84 | 13.00 | 250.00 | 3.62 | NB | 13.43 | NB |

NB = no binding detectable

TABLE 5-continued

Affinity of (biotinylated) SA1_S30K and SA1 control for binding to HSA.

| Test item | $K_D$ (nM) | $k_{on}$ (s$^{-1}$·nM$^{-1}$) | $k_{off}$ (s$^{-1}$) |
|---|---|---|---|
| SA1_S30K | 8.25E−10 | 2.46E+05 | 2.03E−04 |
| SA1_S30K-biotinylated | 1.49E−09 | 1.26E+05 | 1.87E−04 |

Example 6: Cross-Reactivity of SA1_S30K Mutant Variant VHH in Horse, Dog, Cat and Pig The SA1_S30K mutant variant VHH and the original SA1 VHH were shown to bind a number of albumins which are interesting for human and lab animal model serum half-life extension. In order to find out if these VHHs are of use in veterinary applications, they were here tested for binding on dog, cat, horse and pig serum albumins. Bovine albumin proved non-reactive (see Example 4). For these experiments, reference was made to the benchmark HSA Nanobody® (ALB8).

The different albumins were coated on Octet AR2G Biosensors and used to gauge the kinetic binding profile of SA1_S30K, SA1 and ALB8 binding using BioLayer Interferometry (Octet RED96 instrument; Fortebio).

Coating of Albumins on Octet AR2G Tips 10 mg of lyophilized cat, dog, horse or pig serum (HSA) albumin (Sigma) was resuspended in 1 mL of PBS (10 µg/µL). This was used at 20 µg/mL in the "Ligand scouting immobilization conditions" protocol for AR2G Biosensors as detailed in Fortebio Technical Note 26, in conjunction with a Fortebio Octet Red96 machine. Only the pH 5.0 and pH 4.0 condition were tested. The quality of the coating was determined by putting HSA coated tips into contact with a 1000 nM SA1 VHH solution in PBS. In summary, coating of HSA was most efficient at pH 5.0 for cat, horse and pig and at pH 4.0 for horse.

Binding Kinetics Determination

Using the coating conditions described above, 3 columns of 8 AR2G tips were coated with each albumin for the binding study. SA1_S30K, SA1 and ALB8 VHHs were diluted in PBS+0.05% Tween20 at concentrations of 800, 400, 200, 100, 50, 25, 12.5 and 0 nM. These concentrations were brought into contact with the albumin tips for 600 s to measure association and were incubate 900 s in PBS-Tween20 containing wells to measure dissociation.

After data acquisition, the profiles were analyzed using the Octet Data analysis software v9.0. A 1:1 binding model was applied to the values resulting in $K_{on}$, $K_{off}$ and $K_D$ parameters for the experiments involving horse and dog serum albumin (Table 6). No binding could be observed for any of the VHHs on cat and pig serum albumin. On both, horse and dog a $K_D$ of about 100 nM was observed with high off-rates of around $1 \times 10^{-2}$/s for both SA1_S30K and SA1 VHHs. On horse serum albumin, both VHHs have a $K_{on}$ of about $5 \times 10^4$. On dog serum albumin this is slightly higher at $1.5 \times 10^5$. The SA1_S30K and SA1 VHHs have comparable binding profiles on both horse and dog albumins. The ALB8 benchmark VHH did not bind to any of the tested albumins.

Conclusion

The benchmark VHH ALB8 did not bind to cat, dog, horse or pig serum albumin, whereas the original SA1 VHH as well as the mutated variant SA1_S30K showed cross-reactivity to horse and dog serum albumin. Only low affinity with a $K_D$ of about $10^{-7}$ could be observed, which was particularly due to the very high off-rates of around $10^{-2}$/s. The on-rates of $5 \times 10^4$ on horse and $10^5$ on dog serum albumin can be considered as good values though.

TABLE 6

Kinetic binding constants for SA1_S30K, SA1, and ALB8 VHHs on cat (Uniprot P49064), dog (Uniprot P49822), horse (Uniprot P35747) and pig (Uniprot P08835)SA.

| | Horse | | | | | Dog | | | | | | |
|---|---|---|---|---|---|---|---|---|---|---|---|---|
| VHHs | $K_D$ (M) | $k_{on}$ (1/Ms) | $k_{off}$ (1/s) | $X^2$ | $R^2$ | $K_D$ (M) | $k_{on}$ (1/Ms) | $k_{off}$ (1/s) | $X^2$ | $R^2$ | Cat | Pig |
| SA1 | 1,21E−7 | 5,21E+4 | 4,83E−3 | 0,001461 | 0,988 | 1,26E−7 | 1,23E+5 | 1,58E−2 | 0,002899 | 0,966 | NB | NB |
| SA1_S30K | 2,01E−7 | 5,91E+4 | 1,03E−2 | 0,007131 | 0,926 | 1,60E−7 | 1,66E+5 | 1,81E−2 | 0,006389 | 0,926 | NB | NB |
| ALB8 | NB | NB | NB | NB | NB | NB | NB | NB | NB | NB | NB | NB |

Example 7: Pharmaco Kinetics Profile of the SA1_S30K Mutant Variant VHH in Mice To assess the capability of the SA1_S30K variant VHH to extend the half-life of other proteins a fusion protein was generated. The construct consisted of a VHH binding to GFP (Green Fluorescent protein), a GS linker, and the SA1_S30K VHH and is further referred to as VHH-GFP-SA1_S30K (SEQ ID NO:6). This protein was expressed in *Pichia pastoris* and purified from the fermentation medium in a 2-step procedure. After a capturing step via cation exchange (SP Sepharose Fast Flow; GE Healthcare) the protein was polished by size exclusion chromatography (Superdex 75, GE Healthcare) to at least 95% purity of intact protein. Finally, the protein was concentrated to 5 mg/mL in PBS and sterile filtered. Functionality of the fusion protein was confirmed by assessing the affinity for both GPF ($K_D$ 0.5 nM) and human serum albumin ($K_D$ 5 nM).

A PK study was performed in 2 groups of 12 adult male mice (male RjOrl: Swiss CD-1). A first group received a dose of VHH-GFP-SA26 equivalent to 10 mg/kg by intravenous injection. A second group received an identical dose by intraperitoneal injection. Blood samples were taken from 3 animals of each group at the following time points: 0.083 (animals 1-3), 0.25 (animals 4-6), 1 (animals 7-9), 3 (animals 10-12), 8 (animals 1-3), 24 (animals 3-6), 72 (animals 7-9) and 168 (animals 9-12) hours. The K-EDTA blood was stored on ice until centrifugation (10 minutes at 3000×g, 4° C.) and the final plasma samples frozen at −20°. After quantification of the concentration of VHH-GFP-SA26 in each plasma sample (FIG. 3) the terminal half-life was calculated as 30.3 and 36.2 hours for the intravenous and intraperitoneal injection respectively. The half-life at the GFP binding VHH only is assumed to be similar to the typical VHH half-life of 0.5-1.5 h in mouse (Hoefman et al., 2015; Huang et al., 2008) as this VHH is not binding any target in mouse. Hence, these data confirm that the SA1_S30K mutant variant is substantially potent in extending the half-life of other proteins.

Example 8: Humanization of SA1_S30K

To improve the homology with human VH domains the SA1_S30K variant VHH sequence was aligned with the closest human homologue sequence human VH3-23 (GenBank: P01764.2)/J5 (SEQ ID NO:7). Typical residues common in most VHH sequences are often left unchanged as these are considered critical for the VHH properties. However, mutations in framework regions which appear less typical are mutated towards the human amino acid at their respective positions. As non-limiting examples of humanized variants of SEQ ID NO:4, four different humanized sequences were generated for the SA1_S30K variant VHH as provided by SEQ ID NOs: 8-11, including a C-terminal hexahistidine tag for purification (similar to Example 1). All 4 variants were produced and purified according to the method used for the SA1_S30K VHH (see Example 1 and 2), and identified as pure monomers on SDS-PAGE (FIG. 4). Second, their affinity for binding to human and animal serum albumin (as performed in Example 4) was analyzed.

In Table 7, it is shown that no loss in affinity for human or cynomolgus monkey serum albumin was observed, yielding 4 humanized variants suitable for further analysis.

TABLE 7

Serum albumin affinity ($K_D$) of SA1_S30K humanized variants as compared to the SA1_S30K reference.

| | $K_D$ (nM) | |
|---|---|---|
| Sample | human | cyno |
| SA1_S30K | 1.28 | 0.57 |
| SA1_S30K_h1 | 1.33 | 0.36 |
| SA1_S30K_h2 | 1.53 | 0.5 |
| SA1_S30K_h3 | 1.64 | 0.29 |
| SA1_S30K_h4 | 2.11 | 0.32 |

Example 9: Thermal Stability of Humanized SA1_S30K VHH Variants

The thermal stability of the humanized variants was analysed (as performed in Example 3), and revealed that all four humanized variants demonstrate an equal or higher melting temperature ($T_m$) as compared to the SA1_S30K VHH (Table 8).

TABLE 8

Tm of SA1_S30K humanized variants as compared to SA1_S30K reference.

| Sample | $T_m$ (° C.) |
|---|---|
| SA1_S30K | 76.72 |
| SA1_S30K_h1 | 77.54 |
| SA1_S30K_h2 | 80.93 |
| SA1_S30K_h3 | 81 |
| SA1_S30K_h4 | 84.59 |

Looking into more detail, the contribution of 2 amino acid substitutions significantly increased the melting temperature $^{TM}$ and therefore improved thermostability of the humanized variants: an increase of 4° C. in Tm was observed for SA1_S30K_h2 and SA1_S30K_h3, and a total of 8° C. increase was even observed for SA1_S30K_h4 as compared to the SA1_S30K VHH. The substitutions contributing to this raise in thermostability can be derived from FIG. 5: the substitution of Histidine (H) at position 79 (Kabat numbering) to Tyrosine (Y) as well as the substitution of Threonine (T) at position 82b to Serine (S) resulted in a cooperative stabilizing effect on the humanized VHH. Each of the substitutions contributed to an increase in Tm of 4° C. (see h2 and h3), and the combination of both substitutions in h4 resulted in an increase of 8° C. as compared to the SA1_S30K VHH (Table 8).

In conclusion, both H79Y and T82bS increase the melting temperature of the VHH with 4° C., and in combination an increase of 8° C. as compared to the SA1_S30K VHH, showing that at least 3 humanized variants (h2, h3, and h4) demonstrate improved thermostability as compared to the non-humanized sequence.

Example 10: Solubility of Humanized SA1_S30K VHH Variants

The solubility of the VHHs was analysed by 2 different approaches, on the one hand by measurement of the apparent protein solubility by addition of polyethylene glycol (PEG) that precipitates the protein primarily by exclusion volume effects (Toprani et al., JPharmSci, 2016), and on the other hand via measurement of the soluble protein content after repeated freeze-thawing.

The VHH preparations were concentrated using commercial concentration devices (Pierce Concentrator, PES, 3K, MWCO; 5-6 mL). Protein concentration before and after each step was analysed at $OD_{280\,nm}$ on a Nanodrop device.

For the first test, the PEG precipitation test, the VHH samples at 4 mg/mL were mixed with an equal volume of 0, 10, 20 or 40% (w/v) PEG 10000 to achieve final PEG concentrations of 0, 5, 10 and 20% (w/v). After overnight incubation the samples were centrifuged in a 96-well filtration plate (Millipore MultiScreen®HTS GV 0.22 μm hydrophilic Durapore® PVDF membrane), and the filtrate collected for concentration determination ($OD_{280\,nm}$), turbidity ($OD_{320\,nm}$) and aggregation assessment ($OD_{500\,nm}$, $OD_{600\,nm}$). An unfiltered sample was kept to assess turbidity before filtration.

For the second freeze-thaw test, the VHH samples at 3 mg/ml concentration were subjected to 5 freeze (−80° C.) and thaw (RT) cycles (freezing: 4 h or overnight; thawing 1 h). After the $5^{th}$ cycle the $OD_{280\,nm}$, $OD_{320\,nm}$, $OD_{500\,nm}$ and $OD_{600\,nm}$ were measured before and after filtration on 96-well filter plates and compared to a reference sample stored at 4° C. during the time of the freeze-thaw cycling.

TABLE 9

$OD_{280\,nm}$ values for PEG-incubated VHH samples (compared to reference samples)

| | OD 280 nm | | | |
|---|---|---|---|---|
| Sample | 20% PEG | 10% PEG | 5% PEG | 0% PEG |
| SA1_S30K_h1 | 1.030 | 1.054 | 1.050 | 0.981 |
| SA1_S30K_h2 | 1.093 | 1.088 | 1.077 | 1.029 |
| SA1_S30K_h3 | 1.125 | 1.097 | 1.091 | 1.034 |

TABLE 9-continued

OD$_{280\,nm}$ values for PEG-incubated VHH samples (compared to reference samples)

| Sample | OD 280 nm | | | |
|---|---|---|---|---|
| | 20% PEG | 10% PEG | 5% PEG | 0% PEG |
| SA1_S30K_h4 | 1.112 | 1.104 | 1.090 | 1.022 |
| SA1_S30K | 1.064 | 1.059 | 1.065 | 1.030 |

Table 9 demonstrates that no major differences were observed between the various VHHs with respect to solubility using the PEG water exclusion test when testing the VHHs at concentrations of up to 1.5 mg/mL end concentration.

TABLE 10

OD$_{280\,nm}$ and OD$_{320\,nm}$ values for Freeze-thaw cycled samples (compared to reference samples)

| Sample | OD280 | OD320 |
|---|---|---|
| SA1_S30K_h1 | 0.778 | 1.097 |
| SA1_S30K_h2 | 0.759 | 1.065 |
| SA1_S30K_h3 | 0.777 | 1.078 |
| SA1_S30K_h4 | 1.073 | 1.053 |
| SA1_S30K | 0.604 | 1.066 |

Table 10 shows that also for the freeze/thaw cycling no differences were noted between the VHH samples. So, in conclusion the solubility of all humanized variants is at least as high as for the SA1_S30K VHH.

REFERENCES

Bessire et al., 2016. Determination of Antibody-Drug Conjugate Released Payload Species Using Directed in Vitro Assays and Mass Spectrometric Interrogation. Bioconjugate Chem. 27:1645-1654.

Chothia, C., Lesk, A M. 1987. Canonical structures for the hypervariable regions of immunoglobulins. J Mol Biol. 196:901-17.

Chaudhury et al. 2003. The Major Histocompatibility Complex-related Fc Receptor for IgG (FcRn) Binds Albumin and Prolongs Its Lifespan J. Exp. Med. 3, 197: 315-322.

Conrath et al. 2001. Camel single-domain antibodies as modular building units in bispecific and bivalent antibody constructs. J. Biol. Chem. 276: 7346-7350.

Fang, T., Duarte, J. N., Ling, J., Li, Z., Guzman, J. S., Ploegh, H. L. 2016. Structurally Defined aMHC-II Nanobody-Drug Conjugates: A Therapeutic and Imaging System for B-Cell Lymphoma. Angew. Chem. Int. Ed., 55: 2416.

Ghahroudi M A, Desmyter A, Wyns L, Hamers R, Muyldermans S. 1997. Selection and identification of single-domain antibody fragments from camel heavy-chain antibodies. FEBS Lett. 414:521-526.

Hamers-Casterman et al. 1993. Naturally occurring antibodies devoid of light chains. Nature. 363:446-448.

Hoefman et al. 2015. Pre-Clinical Intravenous Serum Pharmacokinetics of Albumin Binding and Non-Half-Life Extended Nanobodies® Antibodies. 4:141-156.

Kabat, E., Wu, T., Foeller, C,. Perry, H., Gottesman K. 1991. Sequences of Proteins of Immunological Interest. 5$^{th}$ edition, NIH publication 91-3242.

Kontermann R E. 2009. Strategies to extend plasma half-lives of recombinant antibodies. BioDrugs. 23:93-109.

Kontermann. 2016. Half-life extended biotherapeutics. Expert Opin Biol Ther. 16(7):903-15.

Kurtzman. 2009. Biotechnological strains of Komagataella (Pichia) pastoris are Komagataella phaffii as determined from multigene sequence analysis. J Ind Microbiol Biotechnol. 36(11): 1435-8.

Lefranc, M-P. (2014). Immunoglobulin and T cell receptor genes: IMGT® and the birth of immunoinformatics. Frontiers in Immunology. 5 (22): 1-22.

Lefranc and Lefranc (2001). The Immunoglobulin Facts-Book. San Diego, Calif., Academic Press.

Lu, J. et al. 2016. Linkers Having a Crucial Role in Antibody-Drug Conjugates. Int J Mol Sci. 17(4):561.

MacCallum et al. 1996. Antibody-antigen interactions: contact analysis and binding site topography. J. Mol. Biol. 262:732-745.

McCombs, J R. and Owen, S. C. 2015. Antibody Drug Conjugates: Design and Selection of Linker, Payload and Conjugation Chemistry. AAPS J. 17(2): 339-351.

Huang L. et al. 2008. SPECT imaging with 99mTc-labeled EGFR-specific nanobody for in vivo monitoring of EGFR expression. Mol. Imaging Biol. 10(3):167-175.

Pillow, T. H. 2017. Novel Linkers and Connections for Antibody-Drug Conjugates to Treat Cancer and Infectious Disease. Pharm Pat Anal. 6(1):25-33.

Roopenian D C, Akilesh S. 2007. FcRn the neonatal Fc receptor comes of age. Nat Rev Immunol. 7:715-725.

Roovers R C, et al. 2007. Efficient inhibition of EGFR signalling and of tumour growth by antagonistic anti-EGFR Nanobody®. Cancer Immunol Immunother. 56:303-317.

Toprani et al. 2016. A Micro-Polyethylene Glycol Precipitation Assay as a Relative Solubility Screening Tool for Monoclonal Antibody Design and Formulation Development. J Pharm Sci. 105(8):2319-27.

The invention claimed is:

1. A polypeptide comprising an immunoglobulin variable domain (IVD),
   wherein the IVD binds to serum albumin,
   wherein the amino acid sequence of the IVD comprises the following structure: FR1-CDR1-FR2-CDR2-FR3-CDR3-FR4, and
   wherein the 3 complementarity determining regions (CDRs) are the CDR1, CDR2, and CDR3 regions as present in SEQ ID NO: 4 as annotated according to MacCallum, IMGT, AbM, or Chothia.

2. The polypeptide of claim 1, wherein CDR1 comprises SEQ ID NO:1, CDR2 comprises SEQ ID NO:2 and CDR3 comprises SEQ ID NO:3.

3. The polypeptide of claim 1,
   wherein the amino acid sequence of the Framework 3 (FR3) region corresponds to the FR3 sequence of SEQ ID NO:4, or to the FR3 sequence of a humanized variant of SEQ ID NO:4
   wherein the amino acid (according to Kabat numbering) of the humanized variant at position 73 and 74 is any amino acid, the amino acid at position 78 is V or L, the amino acid at position 79 is H or Y, and/or the amino acid at position 82b is T or S.

4. The polypeptide of claim 1, wherein the polypeptide comprises SEQ ID NO:4 or a humanized variant of SEQ ID NO:4.

5. The polypeptide of claim 4, wherein the humanized variant of SEQ ID NO:4 is SEQ ID NO: 8, 9, 10, 11, 15, 16, or 17.

6. The polypeptide of claim 5, wherein the humanized variant comprises SEQ ID NO: 4, 8, 9, 10, 11, 15, 16, or 17 substituted in at least one additional amino acid (according to Kabat numbering) at: position 1 to E or D, position 5 to V, position 14 to P, position 73 to any amino acid, position 74 to any amino acid, position 78 to L, or position 108 to L.

7. The polypeptide of claim 5, wherein the humanized variant comprises SEQ ID NO: 4, 8, 9, 10, 11, 15, 16, or 17 substituted in at least one additional amino acid (according to Kabat numbering) at: position 1 to E or D, position 5 to V, position 11 to V, position 13 to K, position 14 to P, position 16 to R, position 73 to any amino acid, position 74 to any amino acid, position 89 to L, or position 108 to Q.

8. The polypeptide of claim 1, wherein the FR3 amino acid (according to Kabat numbering) at position 79 is Y and/or at position 82b is S.

9. The polypeptide of claim 1, wherein the polypeptide is an IVD conjugate, wherein the IVD is coupled via the Lysine residue of CDR1.

10. The polypeptide of claim 9, wherein the IVD conjugate comprises the IVD conjugated to a moiety, wherein the moiety is selected from an enzyme capable of converting a prodrug into a toxic drug, a therapeutic, a cytotoxic drug, an antibody drug-conjugate, and a payload.

11. A therapeutic agent with increased serum half-life,
    wherein the agent comprises the polypeptide of claim 1 and a therapeutic moiety, and
    wherein the half-life of the therapeutic agent is longer as compared to the half-life of the therapeutic moiety without the polypeptide.

12. A multispecific construct comprising the polypeptide according to claim 1 and at least one therapeutic moiety.

13. The multi specific construct of claim 12, wherein the therapeutic moiety comprises an IVD, an immunoglobulin single variable domain, or a fragment thereof.

14. The multispecific construct of claim 12, wherein the polypeptide is linked to the at least one therapeutic moiety via a linker or spacer.

15. A nucleic acid, wherein the nucleic acid encodes the polypeptide of claim 1 or wherein the nucleic acid encodes a multispecific construct comprising the polypeptide according to claim 1.

16. A pharmaceutical composition comprising:
    at least one of:
    a polypeptide according of claim 1 and at least one pharmaceutically acceptable carrier, diluent, or excipient,
    a therapeutic agent comprising the polypeptide of claim 1 and a therapeutic moiety and at least one pharmaceutically acceptable carrier, diluent, or excipient, or
    a multispecific construct comprising the polypeptide according of claim 1 and at least one therapeutic moiety, and at least one pharmaceutically acceptable carrier, diluent or excipient.

* * * * *

SEQUENCE LISTING

<160> NUMBER OF SEQ ID NOS: 157

<210> SEQ ID NO 1
<211> LENGTH: 6
<212> TYPE: PRT
<213> ORGANISM: Artificial Sequence
<220> FEATURE:
<223> OTHER INFORMATION: CDR1 of SA1_S30K

<400> SEQUENCE: 1

Lys Glu Tyr Val Met Gly
1               5

<210> SEQ ID NO 2
<211> LENGTH: 13
<212> TYPE: PRT
<213> ORGANISM: Artificial Sequence
<220> FEATURE:
<223> OTHER INFORMATION: CDR2 of SA1_S30K

<400> SEQUENCE: 2

Phe Val Ala Ala Ile Ser Trp Ser Ala Gly Asn Ile Tyr
1               5                   10

<210> SEQ ID NO 3
<211> LENGTH: 16
<212> TYPE: PRT
<213> ORGANISM: Artificial Sequence
<220> FEATURE:
<223> OTHER INFORMATION: CDR3 of SA1_S30K

<400> SEQUENCE: 3

Ala Ala Gly Arg Tyr Ser Ala Trp Tyr Val Ala Tyr Glu Tyr Asp
1               5                   10                  15

<210> SEQ ID NO 4
<211> LENGTH: 124
<212> TYPE: PRT
<213> ORGANISM: Artificial Sequence
<220> FEATURE:
<223> OTHER INFORMATION: Full length SA1_S30K

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
        35                  40                  45

Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ala Lys Asn Thr Val His
65                  70                  75                  80

Leu Gln Met Asn Thr Leu Arg Pro Glu Asp Thr Ala Val Tyr Tyr Cys
                85                  90                  95

Ala Ala Gly Arg Tyr Ser Ala Trp Tyr Val Ala Tyr Glu Tyr Asp
            100                 105                 110

Tyr Trp Gly Gln Gly Thr Gln Val Thr Val Ser Ser
        115                 120

<210> SEQ ID NO 5
<211> LENGTH: 124
<212> TYPE: PRT
<213> ORGANISM: Artificial Sequence
<220> FEATURE:
<223> OTHER INFORMATION: Full length SA1

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Asn Ile Ser Glu Tyr
            20                  25                  30

Val Met Gly Trp Phe Arg Gln Ala Pro Gly Lys Glu Arg Glu Phe Val
        35                  40                  45

```
Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ala Lys Asn Thr Val His
 65                  70                  75                  80

Leu Gln Met Asn Thr Leu Arg Pro Glu Asp Thr Ala Val Tyr Tyr Cys
                 85                  90                  95

Ala Ala Gly Arg Tyr Ser Ala Trp Tyr Val Ala Ala Tyr Glu Tyr Asp
            100                 105                 110

Tyr Trp Gly Gln Gly Thr Gln Val Thr Val Ser Ser
            115                 120

<210> SEQ ID NO 6
<211> LENGTH: 299
<212> TYPE: PRT
<213> ORGANISM: Artificial Sequence
<220> FEATURE:
<223> OTHER INFORMATION: Full length VHH-GFP-SA1_S30K

<400> SEQUENCE: 6

Gln Val Gln Leu Gln Glu Ser Gly Gly Ala Leu Val Gln Pro Gly Gly
 1               5                  10                  15

Ser Leu Arg Leu Ser Cys Ala Ala Ser Gly Phe Pro Val Asn Arg Tyr
                20                  25                  30

Ser Met Arg Trp Tyr Arg Gln Ala Pro Gly Lys Glu Arg Glu Trp Val
             35                  40                  45

Ala Gly Met Ser Ser Ala Gly Asp Arg Ser Ser Tyr Glu Asp Ser Val
     50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
             100                 105                 110

Val Ser Ser Gly Gly Ser Gly Gly Ser Gly Gly Ser Gly Gly Ser Gly
            115                 120                 125

Gly Ser Gly Gly Ser Gly Gly Ser Gly Gly Ser Gly Gly Ser Gly Gly
    130                 135                 140

Ser Gly Gly Ser Gly Gly Ser Gly Gly Ser Gly Gly Ser Gly Gly Ser
145                 150                 155                 160

Gly Gly Ser Gly Gly Ser Gly Gly Ser Gly Gly Ser Gly Gly Ser Gln
                165                 170                 175

Val Gln Leu Gln Glu Ser Gly Gly Leu Val Gln Ala Gly Gly Ser
            180                 185                 190

Leu Arg Leu Ser Cys Ala Ala Ser Gly Arg Asn Ile Lys Glu Tyr Val
            195                 200                 205

Met Gly Trp Phe Arg Gln Ala Pro Gly Lys Glu Arg Glu Phe Val Ala
    210                 215                 220

Ala Ile Ser Trp Ser Ala Gly Asn Ile Tyr Tyr Ala Asp Ser Val Lys
225                 230                 235                 240

Gly Arg Phe Thr Ile Ser Arg Asp Asn Ala Lys Asn Thr Val His Leu
                245                 250                 255

Gln Met Asn Thr Leu Arg Pro Glu Asp Thr Ala Val Tyr Tyr Cys Ala
            260                 265                 270

Ala Gly Arg Tyr Ser Ala Trp Tyr Val Ala Ala Tyr Glu Tyr Asp Tyr
            275                 280                 285
```

```
Trp Gly Gln Gly Thr Gln Val Thr Val Ser Ser
        290                 295

<210> SEQ ID NO 7
<211> LENGTH: 109
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 8
<211> LENGTH: 124
<212> TYPE: PRT
<213> ORGANISM: Artificial Sequence
<220> FEATURE:
<223> OTHER INFORMATION: SA1_S30K_human1

<400> SEQUENCE: 8

Glu Val Gln Leu Gln Glu Ser Gly Gly Gly Leu Val Gln Pro Gly Gly
1               5                   10                  15

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
        35                  40                  45

Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ser Lys Asn Thr Val His
65                  70                  75                  80

Leu Gln Met Asn Thr Leu Arg Pro Glu Asp Thr Ala Val Tyr Tyr Cys
                85                  90                  95

Ala Ala Gly Arg Tyr Ser Ala Trp Tyr Val Ala Ala Tyr Glu Tyr Asp
            100                 105                 110

Tyr Trp Gly Gln Gly Thr Leu Val Thr Val Ser Ser
        115                 120

<210> SEQ ID NO 9
<211> LENGTH: 124
<212> TYPE: PRT
<213> ORGANISM: Artificial Sequence
<220> FEATURE:
<223> OTHER INFORMATION: SA1_S30K_human2

<400> SEQUENCE: 9

Glu Val Gln Leu Gln Glu Ser Gly Gly Gly Leu Val Gln Pro Gly Gly
1               5                   10                  15
```

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
        35                  40                  45

Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Thr Leu Arg Pro Glu Asp Thr Ala Val Tyr Tyr Cys
                85                  90                  95

Ala Ala Gly Arg Tyr Ser Ala Trp Tyr Val Ala Ala Tyr Glu Tyr Asp
            100                 105                 110

Tyr Trp Gly Gln Gly Thr Leu Val Thr Val Ser Ser
            115                 120

<210> SEQ ID NO 10
<211> LENGTH: 124
<212> TYPE: PRT
<213> ORGANISM: Artificial Sequence
<220> FEATURE:
<223> OTHER INFORMATION: SA1_S30K_human3

<400> SEQUENCE: 10

Glu Val Gln Leu Gln Glu Ser Gly Gly Gly Leu Val Gln Pro Gly Gly
1               5                   10                  15

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
        35                  40                  45

Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ser Lys Asn Thr Val His
65                  70                  75                  80

Leu Gln Met Asn Ser Leu Arg Pro Glu Asp Thr Ala Val Tyr Tyr Cys
                85                  90                  95

Ala Ala Gly Arg Tyr Ser Ala Trp Tyr Val Ala Ala Tyr Glu Tyr Asp
            100                 105                 110

Tyr Trp Gly Gln Gly Thr Leu Val Thr Val Ser Ser
            115                 120

<210> SEQ ID NO 11
<211> LENGTH: 124
<212> TYPE: PRT
<213> ORGANISM: Artificial Sequence
<220> FEATURE:
<223> OTHER INFORMATION: SA1_S30K_human4

<400> SEQUENCE: 11

Glu Val Gln Leu Gln Glu Ser Gly Gly Gly Leu Val Gln Pro Gly Gly
1               5                   10                  15

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
        35                  40                  45

Ala Ala Ile Ser Trp Ser Ala Gly Asn Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

-continued

```
Leu Gln Met Asn Ser Leu Arg Pro Glu Asp Thr Ala Val Tyr Tyr Cys
                85                  90                  95
Ala Ala Gly Arg Tyr Ser Ala Trp Tyr Val Ala Ala Tyr Glu Tyr Asp
            100                 105                 110
Tyr Trp Gly Gln Gly Thr Leu Val Thr Val Ser Ser
        115                 120

<210> SEQ ID NO 12
<211> LENGTH: 609
<212> TYPE: PRT
<213> ORGANISM: Homo sapiens

<400> SEQUENCE: 12

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
            20                  25                  30
His Arg Phe Lys Asp Leu Gly Glu Glu Asn Phe Lys Ala Leu Val Leu
        35                  40                  45
Ile Ala Phe Ala Gln Tyr Leu Gln Gln Cys Pro Phe Glu Asp His Val
    50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
        115                 120                 125
His Lys Asp Asp Asn Pro Asn Leu Pro Arg Leu Val Arg Pro Glu Val
    130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
            180                 185                 190
Cys Gln Ala Ala Asp Lys Ala Ala Cys Leu Leu Pro Lys Leu Asp Glu
        195                 200                 205
Leu Arg Asp Glu Gly Lys Ala Ser Ser Ala Lys Gln Arg Leu Lys Cys
    210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
```

```
                    325                 330                 335
Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 13
<211> LENGTH: 608
<212> TYPE: PRT
<213> ORGANISM: Mus musculus

<400> SEQUENCE: 13

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
```

-continued

```
                85                  90                  95
Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
            115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
            275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
            435                 440                 445

Glu Ala Ala Arg Asn Leu Gly Arg Val Gly Thr Lys Cys Cys Thr Leu
    450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
            500                 505                 510
```

-continued

Ser Ala Leu Thr Val Asp Glu Thr Tyr Val Pro Lys Glu Phe Lys Ala
            515                 520                 525

Glu Thr Phe Thr Phe His Ser Asp Ile Cys Thr Leu Pro Glu Lys Glu
        530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Ala Leu Ala
        595                 600                 605

<210> SEQ ID NO 14
<211> LENGTH: 608
<212> TYPE: PRT
<213> ORGANISM: Rattus norvegicus

<400> SEQUENCE: 14

Met Lys Trp Val Thr Phe Leu Leu Leu Leu Phe Ile Ser Gly Ser Ala
1               5                   10                  15

Phe Ser Arg Gly Val Phe Arg Arg Glu Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Tyr Leu Gln Lys Cys Pro Tyr Glu Glu His Ile
    50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Phe Gln Arg Pro Glu Ala
    130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
        195                 200                 205

Val Lys Glu Lys Ala Leu Val Ala Ala Val Arg Gln Arg Met Lys Cys
    210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
                245                 250                 255

Lys Leu Ala Thr Asp Val Thr Lys Ile Asn Lys Glu Cys Cys His Gly
            260                 265                 270

Asp Leu Leu Glu Cys Ala Asp Asp Arg Ala Glu Leu Ala Lys Tyr Met

```
                    275                 280                 285
        Cys Glu Asn Gln Ala Thr Ile Ser Ser Lys Leu Gln Ala Cys Cys Asp
            290                 295                 300
        Lys Pro Val Leu Gln Lys Ser Gln Cys Leu Ala Glu Ile Glu His Asp
        305                 310                 315                 320
        Asn Ile Pro Ala Asp Leu Pro Ser Ile Ala Ala Asp Phe Val Glu Asp
                        325                 330                 335
        Lys Glu Val Cys Lys Asn Tyr Ala Glu Ala Lys Asp Val Phe Leu Gly
                    340                 345                 350
        Thr Phe Leu Tyr Glu Tyr Ser Arg Arg His Pro Asp Tyr Ser Val Ser
                355                 360                 365
        Leu Leu Leu Arg Leu Ala Lys Lys Tyr Glu Ala Thr Leu Glu Lys Cys
            370                 375                 380
        Cys Ala Glu Gly Asp Pro Pro Ala Cys Tyr Gly Thr Val Leu Ala Glu
        385                 390                 395                 400
        Phe Gln Pro Leu Val Glu Glu Pro Lys Asn Leu Val Lys Thr Asn Cys
                        405                 410                 415
        Glu Leu Tyr Glu Lys Leu Gly Glu Tyr Gly Phe Gln Asn Ala Val Leu
                    420                 425                 430
        Val Arg Tyr Thr Gln Lys Ala Pro Gln Val Ser Thr Pro Thr Leu Val
                435                 440                 445
        Glu Ala Ala Arg Asn Leu Gly Arg Val Gly Thr Lys Cys Cys Thr Leu
            450                 455                 460
        Pro Glu Ala Gln Arg Leu Pro Cys Val Glu Asp Tyr Leu Ser Ala Ile
        465                 470                 475                 480
        Leu Asn Arg Leu Cys Val Leu His Glu Lys Thr Pro Val Ser Glu Lys
                        485                 490                 495
        Val Thr Lys Cys Cys Ser Gly Ser Leu Val Glu Arg Arg Pro Cys Phe
                    500                 505                 510
        Ser Ala Leu Thr Val Asp Glu Thr Tyr Val Pro Lys Glu Phe Lys Ala
                515                 520                 525
        Glu Thr Phe Thr Phe His Ser Asp Ile Cys Thr Leu Pro Asp Lys Glu
            530                 535                 540
        Lys Gln Ile Lys Lys Gln Thr Ala Leu Ala Glu Leu Val Lys His Lys
        545                 550                 555                 560
        Pro Lys Ala Thr Glu Asp Gln Leu Lys Thr Val Met Gly Asp Phe Ala
                        565                 570                 575
        Gln Phe Val Asp Lys Cys Cys Lys Ala Ala Asp Lys Asp Asn Cys Phe
                    580                 585                 590
        Ala Thr Glu Gly Pro Asn Leu Val Ala Arg Ser Lys Glu Ala Leu Ala
                595                 600                 605

<210> SEQ ID NO 15
<211> LENGTH: 124
<212> TYPE: PRT
<213> ORGANISM: Artificial Sequence
<220> FEATURE:
<223> OTHER INFORMATION: humanized variant h5 of SA1_S30K

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Asn Ile Lys Glu Tyr
            20                  25                  30

Val Met Gly Trp Phe Arg Gln Ala Pro Gly Lys Glu Arg Glu Phe Val
```

```
                35                  40                  45
Ala Ala Ile Ser Trp Ser Ala Gly Asn Ile Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Thr Leu Arg Pro Glu Asp Thr Ala Val Tyr Tyr Cys
                 85                  90                  95

Ala Ala Gly Arg Tyr Ser Ala Trp Tyr Val Ala Ala Tyr Glu Tyr Asp
                100                 105                 110

Tyr Trp Gly Gln Gly Thr Gln Val Thr Val Ser Ser
            115                 120

<210> SEQ ID NO 16
<211> LENGTH: 124
<212> TYPE: PRT
<213> ORGANISM: Artificial Sequence
<220> FEATURE:
<223> OTHER INFORMATION: humanized variant h6 of SA1_S30K

<400> SEQUENCE: 16

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Asn Ile Lys Glu Tyr
                20                  25                  30

Val Met Gly Trp Phe Arg Gln Ala Pro Gly Lys Glu Arg Glu Phe Val
                35                  40                  45

Ala Ala Ile Ser Trp Ser Ala Gly Asn Ile Tyr Tyr Ala Asp Ser Val
 50                  55                  60

Lys Gly Arg Phe Thr Ile Ser Arg Asp Asn Ala Lys Asn Thr Val His
 65                  70                  75                  80

Leu Gln Met Asn Ser Leu Arg Pro Glu Asp Thr Ala Val Tyr Tyr Cys
                 85                  90                  95

Ala Ala Gly Arg Tyr Ser Ala Trp Tyr Val Ala Ala Tyr Glu Tyr Asp
                100                 105                 110

Tyr Trp Gly Gln Gly Thr Gln Val Thr Val Ser Ser
            115                 120

<210> SEQ ID NO 17
<211> LENGTH: 124
<212> TYPE: PRT
<213> ORGANISM: Artificial Sequence
<220> FEATURE:
<223> OTHER INFORMATION: humanized variant h7 of SA1_S30K

<400> SEQUENCE: 17

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Asn Ile Lys Glu Tyr
                20                  25                  30

Val Met Gly Trp Phe Arg Gln Ala Pro Gly Lys Glu Arg Glu Phe Val
                35                  40                  45

Ala Ala Ile Ser Trp Ser Ala Gly Asn Ile Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95
```

Ala Ala Gly Arg Tyr Ser Ala Trp Tyr Val Ala Ala Tyr Glu Tyr Asp
            100                 105                 110

Tyr Trp Gly Gln Gly Thr Gln Val Thr Val Ser Ser
        115                 120

<210> SEQ ID NO 18
<211> LENGTH: 37
<212> TYPE: PRT
<213> ORGANISM: Artificial Sequence
<220> FEATURE:
<223> OTHER INFORMATION: FR3 from SA1_S30K
<220> FEATURE:
<221> NAME/KEY: misc_feature
<222> LOCATION: (15)..(16)
<223> OTHER INFORMATION: Xaa can be any naturally occurring amino acid

<400> SEQUENCE: 18

Tyr Ala Asp Ser Val Lys Gly Arg Phe Thr Ile Ser Arg Asp Xaa Xaa
1               5                   10                  15

Lys Asn Thr Val His Leu Gln Met Asn Thr Leu Arg Pro Glu Asp Thr
            20                  25                  30

Ala Val Tyr Tyr Cys
        35

<210> SEQ ID NO 19
<211> LENGTH: 98
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 20
<211> LENGTH: 98
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg

<210> SEQ ID NO 21
<211> LENGTH: 98
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
                35                  40                  45

Ala Asn Ile Lys Gln Asp Gly Ser Glu Lys Tyr Tyr Val Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 22
<211> LENGTH: 99
<212> TYPE: PRT
<213> ORGANISM: Homo sapiens

<400> SEQUENCE: 22

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Gly Ile Ser Trp Asn Ser Gly Ser Ile Gly Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 23
<211> LENGTH: 99
<212> TYPE: PRT
<213> ORGANISM: Homo sapiens

<400> SEQUENCE: 23

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
                20                  25                  30

Ala Met His Trp Val Arg Gln Ala Pro Gly Lys Gly Leu Glu Trp Val
                35                  40                  45
```

```
Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 24
<211> LENGTH: 99
<212> TYPE: PRT
<213> ORGANISM: Homo sapiens

<400> SEQUENCE: 24

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Met Ala Leu Tyr Tyr Cys
                85                  90                  95

Ala Lys Asp

<210> SEQ ID NO 25
<211> LENGTH: 98
<212> TYPE: PRT
<213> ORGANISM: Homo sapiens

<400> SEQUENCE: 25

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 26
<211> LENGTH: 98
<212> TYPE: PRT
<213> ORGANISM: Homo sapiens

<400> SEQUENCE: 26

Gln Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
```

20                  25                  30

Tyr Met Ser Trp Ile Arg Gln Ala Pro Gly Lys Gly Leu Glu Trp Val
            35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 27
<211> LENGTH: 98
<212> TYPE: PRT
<213> ORGANISM: Homo sapiens

<400> SEQUENCE: 27

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 28
<211> LENGTH: 98
<212> TYPE: PRT
<213> ORGANISM: Homo sapiens

<400> SEQUENCE: 28

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 29
<211> LENGTH: 98
<212> TYPE: PRT
<213> ORGANISM: Homo sapiens

<400> SEQUENCE: 29

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 30
<211> LENGTH: 97
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 31
<211> LENGTH: 97
<212> TYPE: PRT
<213> ORGANISM: Homo sapiens

<400> SEQUENCE: 31

Glu Val His Leu Val Glu Ser Gly Gly Gly Leu Val Gln Pro Gly Gly
1               5                   10                  15

Ala Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Asn Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 32

<211> LENGTH: 97
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Cys Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Gln Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 33
<211> LENGTH: 97
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 34
<211> LENGTH: 97
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Pro Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 35
<211> LENGTH: 100
<212> TYPE: PRT
<213> ORGANISM: Homo sapiens

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 36
<211> LENGTH: 100
<212> TYPE: PRT
<213> ORGANISM: Homo sapiens

<400> SEQUENCE: 36

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 37
<211> LENGTH: 100
<212> TYPE: PRT
<213> ORGANISM: Homo sapiens

<400> SEQUENCE: 37

Glu Val Gln Leu Val Glu Ser Ala Gly Ala Leu Val Gln Pro Gly Gly
1               5                   10                  15

Ser Leu Arg Leu Ser Cys Ala Ala Ser Gly Phe Thr Cys Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Ala Asn Gly Gly Thr Thr Asp Tyr Ala Ala

```
                    50                  55                  60
Pro Val Lys Gly Arg Phe Thr Ile Ser Arg Val Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 38
<211> LENGTH: 100
<212> TYPE: PRT
<213> ORGANISM: Homo sapiens

<400> SEQUENCE: 38

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Glu Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 39
<211> LENGTH: 100
<212> TYPE: PRT
<213> ORGANISM: Homo sapiens

<400> SEQUENCE: 39

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 40
<211> LENGTH: 100
<212> TYPE: PRT
<213> ORGANISM: Homo sapiens

<400> SEQUENCE: 40

Glu Val Gln Leu Val Glu Ser Gly Gly Gly Leu Val Lys Pro Gly Gly
  1               5                  10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asn Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 41
<211> LENGTH: 100
<212> TYPE: PRT
<213> ORGANISM: Homo sapiens

<400> SEQUENCE: 41

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 42
<211> LENGTH: 100
<212> TYPE: PRT
<213> ORGANISM: Homo sapiens

<400> SEQUENCE: 42

Glu Val Gln Leu Val Glu Ser Ala Gly Gly Leu Val Gln Pro Gly Gly
 1               5                  10                  15

Ser Leu Arg Leu Ser Cys Ala Ala Ser Gly Phe Thr Cys Ser Asn Ala
            20                  25                  30

Trp Met Ser Trp Val Arg Gln Ala Pro Gly Lys Gly Leu Glu Trp Val
        35                  40                  45

Gly Cys Ile Lys Ser Lys Ala Asn Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Ile Ser Leu Lys Thr Glu Asp Thr Ala Val Tyr
                85                  90                  95

Tyr Cys Thr Thr
            100

<210> SEQ ID NO 43
```

```
<211> LENGTH: 98
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 44
<211> LENGTH: 98
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 45
<211> LENGTH: 98
<212> TYPE: PRT
<213> ORGANISM: Homo sapiens

<400> SEQUENCE: 45

Thr Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Phe Leu Tyr
65                  70                  75                  80

Gln Gln Met Asn Ser Leu Arg Pro Glu Asp Met Ala Val Tyr Tyr Cys
                85                  90                  95
```

Val Arg

<210> SEQ ID NO 46
<211> LENGTH: 98
<212> TYPE: PRT
<213> ORGANISM: Homo sapiens

<400> SEQUENCE: 46

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 47
<211> LENGTH: 98
<212> TYPE: PRT
<213> ORGANISM: Homo sapiens

<400> SEQUENCE: 47

Glu Val Gln Leu Val Glu Ser Gly Gly Gly Val Val Arg Pro Gly Gly
1               5                   10                  15

Ser Leu Arg Leu Ser Phe Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 48
<211> LENGTH: 98
<212> TYPE: PRT
<213> ORGANISM: Homo sapiens

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Ala Asp Ser Val
    50                  55                  60

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 49
<211> LENGTH: 98
<212> TYPE: PRT
<213> ORGANISM: Homo sapiens

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 50
<211> LENGTH: 98
<212> TYPE: PRT
<213> ORGANISM: Homo sapiens

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 51
<211> LENGTH: 98
<212> TYPE: PRT
<213> ORGANISM: Homo sapiens

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val 35                  40                  45
Ser Ser Ile Ser Ser Ser Ser Tyr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 52
<211> LENGTH: 99
<212> TYPE: PRT
<213> ORGANISM: Homo sapiens

<400> SEQUENCE: 52

Glu Val His Leu Val Glu Ser Gly Gly Ala Leu Val Gln Pro Gly Gly
 1               5                  10                  15

Ser Leu Arg Leu Ser Cys Ala Ala Ser Gly Phe Thr Phe Ser Tyr Tyr
                20                  25                  30

Tyr Met Ser Gly Val Arg Gln Ala Pro Gly Lys Gly Leu Glu Trp Val
                35                  40                  45

Gly Phe Ile Arg Asn Lys Ala Asn Gly Gly Thr Thr Glu Tyr Thr Ser
 50                  55                  60

Val Lys Gly Arg Phe Thr Ile Ser Arg Asp Asp Ser Lys Ser Ile Thr
 65                  70                  75                  80

Tyr Leu Gln Met Lys Ser Leu Lys Thr Glu Asp Thr Ala Val Tyr Tyr
                 85                  90                  95

Cys Ser Arg

<210> SEQ ID NO 53
<211> LENGTH: 99
<212> TYPE: PRT
<213> ORGANISM: Homo sapiens

<400> SEQUENCE: 53

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
                20                  25                  30

Tyr Met Ser Gly Val Arg Gln Ala Pro Gly Lys Gly Leu Glu Trp Val
                35                  40                  45

Gly Phe Ile Arg Asn Lys Ala Asn Gly Gly Thr Thr Glu Tyr Thr Ser
 50                  55                  60

Val Lys Gly Arg Phe Thr Ile Ser Arg Asp Asp Ser Lys Ser Ile Thr
 65                  70                  75                  80

Tyr Leu Gln Met Lys Ser Leu Lys Thr Glu Asp Thr Ala Val Tyr Tyr
                 85                  90                  95

Cys Ser Arg

<210> SEQ ID NO 54
<211> LENGTH: 98
<212> TYPE: PRT
<213> ORGANISM: Homo sapiens

<400> SEQUENCE: 54

Glu Val Gln Leu Leu Glu Ser Gly Gly Gly Leu Val Gln Pro Gly Gly
 1               5                  10                  15

-continued

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 55
<211> LENGTH: 98
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 56
<211> LENGTH: 98
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Tyr Ser Gly Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 57
<211> LENGTH: 98
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 58
<211> LENGTH: 98
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Tyr Ser Ser Gly Ser Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 59
<211> LENGTH: 98
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 60
<211> LENGTH: 96
<212> TYPE: PRT
<213> ORGANISM: Homo sapiens

<400> SEQUENCE: 60

Glu Met Gln Leu Val Glu Ser Gly Gly Gly Leu Gln Lys Pro Ala Trp
1               5                   10                  15

Ser Pro Arg Leu Ser Cys Ala Ala Ser Gln Phe Thr Phe Ser Ser Tyr
            20                  25                  30

Tyr Met Asn Cys Val Arg Gln Ala Pro Gly Asn Gly Leu Glu Leu Val
        35                  40                  45

Gln Val Asn Pro Asn Gly Gly Ser Thr Tyr Leu Ile Asp Ser Gly Lys
    50                  55                  60

Asp Arg Phe Asn Thr Ser Arg Asp Asn Ala Lys Asn Thr Leu His Leu
65                  70                  75                  80

Gln Met Asn Ser Leu Lys Thr Glu Asp Thr Ala Leu Tyr Cys Thr Arg
                85                  90                  95

<210> SEQ ID NO 61
<211> LENGTH: 96
<212> TYPE: PRT
<213> ORGANISM: Homo sapiens

<400> SEQUENCE: 61

Glu Met Gln Leu Val Glu Ser Gly Gly Gly Leu Ala Lys Pro Ala Trp
1               5                   10                  15

Ser Pro Arg Leu Ser Cys Ala Ala Ser Gln Phe Thr Phe Ser Ser Tyr
            20                  25                  30

Tyr Met Asn Cys Val Arg Gln Ala Pro Gly Asn Gly Leu Glu Leu Val
        35                  40                  45

Gln Val Asn Pro Asn Gly Gly Ser Thr Tyr Leu Ile Asp Ser Gly Lys
    50                  55                  60

Asp Arg Phe Asn Thr Ser Arg Asp Asn Ala Lys Asn Thr Leu His Leu
65                  70                  75                  80

Gln Met Asn Ser Leu Lys Thr Glu Asp Thr Ala Leu Tyr Cys Thr Arg
                85                  90                  95

<210> SEQ ID NO 62
<211> LENGTH: 97
<212> TYPE: PRT
<213> ORGANISM: Homo sapiens

<400> SEQUENCE: 62

Glu Met Gln Leu Val Glu Ser Gly Gly Gly Leu Ala Lys Pro Ala Trp
1               5                   10                  15

Ser Pro Arg Leu Ser Cys Ala Ala Ser Gln Phe Thr Phe Ser Ser Tyr
            20                  25                  30

Tyr Met Asn Cys Val Arg Gln Ala Pro Gly Asn Gly Leu Glu Leu Val
        35                  40                  45

Gly Gln Val Asn Pro Asn Gly Gly Ser Thr Tyr Leu Ile Asp Ser Gly
    50                  55                  60

Lys Asp Arg Phe Asn Thr Ser Arg Asp Asn Ala Lys Asn Thr Leu His
65                  70                  75                  80

Leu Gln Met Asn Ser Leu Lys Thr Glu Asp Thr Ala Leu Tyr Cys Thr
                85                  90                  95

Arg

<210> SEQ ID NO 63
<211> LENGTH: 98
<212> TYPE: PRT
<213> ORGANISM: Homo sapiens

<400> SEQUENCE: 63

Glu Thr Gln Leu Val Glu Ser Gly Gly Gly Leu Ala Lys Pro Gly Arg
1               5                   10                  15

Ser Pro Arg Leu Ser Cys Ala Ala Ser Gln Phe Thr Phe Ser Ser Tyr
            20                  25                  30

Tyr Met Asn Cys Val Arg Gln Ala Pro Gly Asn Gly Leu Glu Leu Val
        35                  40                  45

Gly Gln Val Asn Pro Asn Gly Gly Ser Thr Tyr Leu Ile Asp Ser Gly
    50                  55                  60

Lys Asp Arg Phe Asn Thr Ser Arg Asp Asn Ala Lys Asn Thr Leu His
65                  70                  75                  80

Leu Gln Met Asn Ser Leu Lys Thr Glu Asp Thr Ala Leu Tyr Tyr Cys
                85                  90                  95

Thr Arg

<210> SEQ ID NO 64
<211> LENGTH: 97
<212> TYPE: PRT
<213> ORGANISM: Homo sapiens

<400> SEQUENCE: 64

Glu Met Gln Leu Val Glu Ser Gly Gly Gly Leu Ala Lys Pro Ala Trp
1               5                   10                  15

Ser Pro Arg Leu Ser Cys Ala Ala Ser Gln Phe Thr Phe Ser Ser Tyr
            20                  25                  30

Tyr Met Asn Cys Val Arg Gln Ala Pro Gly Asn Gly Leu Glu Leu Val
        35                  40                  45

Gly Gln Val Asn Pro Asn Gly Gly Ser Thr Tyr Leu Ile Asp Ser Gly
    50                  55                  60

Lys Asp Arg Phe Asn Thr Ser Arg Asp Asn Ala Lys Asn Thr Leu His
65                  70                  75                  80

Leu Gln Met Asn Ser Leu Lys Thr Glu Asp Thr Ala Leu Tyr Cys Thr
                85                  90                  95

Arg

<210> SEQ ID NO 65
<211> LENGTH: 96
<212> TYPE: PRT
<213> ORGANISM: Homo sapiens

<400> SEQUENCE: 65

Glu Val Glu Leu Ile Glu Pro Thr Glu Asp Leu Arg Gln Pro Gly Lys
1               5                   10                  15

Phe Leu Arg Leu Ser Cys Val Ala Ser Arg Phe Ala Phe Ser Ser Phe
            20                  25                  30

Met Ser Pro Val His Gln Ser Ala Gly Lys Gly Leu Glu Val Ile Asp
        35                  40                  45

Ile Lys Asp Asp Gly Ser Gln Ile His His Ala Asp Ser Val Lys Gly
    50                  55                  60

Arg Phe Ser Ile Ser Lys Asp Asn Ala Lys Asn Ser Leu Tyr Leu Gln
65                  70                  75                  80

Met Asn Ser Gln Arg Thr Glu Asp Met Ala Val Tyr Gly Cys Thr Gly
                85                  90                  95

<210> SEQ ID NO 66
<211> LENGTH: 98
<212> TYPE: PRT
<213> ORGANISM: Homo sapiens

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 67
<211> LENGTH: 98
<212> TYPE: PRT
<213> ORGANISM: Homo sapiens

<400> SEQUENCE: 67

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 68
<211> LENGTH: 98
<212> TYPE: PRT
<213> ORGANISM: Homo sapiens

<400> SEQUENCE: 68

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 69
<211> LENGTH: 98
<212> TYPE: PRT
<213> ORGANISM: Homo sapiens

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Gly Thr Ala Val Tyr Tyr Cys
                 85                  90                  95

Ala Arg

<210> SEQ ID NO 70
<211> LENGTH: 98
<212> TYPE: PRT
<213> ORGANISM: Homo sapiens

<400> SEQUENCE: 70

Gln Val Gln Leu Val Asp Ser Gly Gly Gly Val Val Gln Pro Gly Arg
1               5                   10                  15

Ser Leu Arg Leu Ser Cys Ala Ala Ser Ala Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 71
<211> LENGTH: 98
<212> TYPE: PRT
<213> ORGANISM: Homo sapiens

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                 20                  25                  30
```

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 72
<211> LENGTH: 98
<212> TYPE: PRT
<213> ORGANISM: Homo sapiens

<400> SEQUENCE: 72

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 73
<211> LENGTH: 98
<212> TYPE: PRT
<213> ORGANISM: Homo sapiens

<400> SEQUENCE: 73

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 74
<211> LENGTH: 98
<212> TYPE: PRT
<213> ORGANISM: Homo sapiens

<400> SEQUENCE: 74

Gln Val Gln Leu Val Glu Ser Gly Gly Gly Val Val Gln Pro Gly Arg

```
1               5                   10                  15
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 75
<211> LENGTH: 98
<212> TYPE: PRT
<213> ORGANISM: Homo sapiens

<400> SEQUENCE: 75

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 76
<211> LENGTH: 98
<212> TYPE: PRT
<213> ORGANISM: Homo sapiens

<400> SEQUENCE: 76

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg
```

<210> SEQ ID NO 77
<211> LENGTH: 98
<212> TYPE: PRT

<213> ORGANISM: Homo sapiens

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 78
<211> LENGTH: 98
<212> TYPE: PRT
<213> ORGANISM: Homo sapiens

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 79
<211> LENGTH: 98
<212> TYPE: PRT
<213> ORGANISM: Homo sapiens

<400> SEQUENCE: 79

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 80
<211> LENGTH: 98
<212> TYPE: PRT
<213> ORGANISM: Homo sapiens

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 81
<211> LENGTH: 98
<212> TYPE: PRT
<213> ORGANISM: Homo sapiens

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 82
<211> LENGTH: 98
<212> TYPE: PRT
<213> ORGANISM: Homo sapiens

<400> SEQUENCE: 82

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 83
<211> LENGTH: 98
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 84
<211> LENGTH: 98
<212> TYPE: PRT
<213> ORGANISM: Homo sapiens

<400> SEQUENCE: 84

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 85
<211> LENGTH: 98
<212> TYPE: PRT
<213> ORGANISM: Homo sapiens

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 86
<211> LENGTH: 98
<212> TYPE: PRT
<213> ORGANISM: Homo sapiens

<400> SEQUENCE: 86

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 87
<211> LENGTH: 95
<212> TYPE: PRT
<213> ORGANISM: Homo sapiens

<400> SEQUENCE: 87

Glu Val Gln Leu Val Glu Ser Gly Glu Asp Pro Arg Gln Pro Gly Gly
 1               5                  10                  15

Ser Leu Arg Leu Ser Cys Ala Asp Ser Gly Leu Thr Phe Ser Ser Tyr
                20                  25                  30

Arg Asn Ser Val Ser Gln Ala Pro Gly Lys Gly Leu Glu Val Val Asp
            35                  40                  45

Ile Gln Cys Asp Gly Ser Gln Ile Cys Tyr Ala Ser Leu Lys Ser Lys
            50                  55                  60

Phe Thr Ile Ser Lys Glu Asn Ala Lys Asn Ser Leu Tyr Leu Leu Met
 65                  70                  75                  80

Asn Ser Leu Arg Ala Ala Gly Thr Ala Val Cys Tyr Cys Met Gly
                 85                  90                  95

<210> SEQ ID NO 88
<211> LENGTH: 98
<212> TYPE: PRT
<213> ORGANISM: Homo sapiens

<400> SEQUENCE: 88

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 89
<211> LENGTH: 98
<212> TYPE: PRT
<213> ORGANISM: Homo sapiens

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 90
<211> LENGTH: 98
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 91
<211> LENGTH: 96
<212> TYPE: PRT
<213> ORGANISM: Homo sapiens

<400> SEQUENCE: 91

Glu Val Glu Leu Ile Glu Ser Ile Glu Asp Leu Arg Gln Pro Gly Lys

```
                1               5                   10                  15
            Phe Leu Arg Leu Ser Cys Val Ala Ser Arg Phe Ala Phe Ser Ser Phe
                            20                  25                  30

Met Ser Arg Val His Gln Ser Pro Gly Lys Gly Leu Glu Val Ile Asp
                        35                  40                  45

Ile Lys Asp Asp Gly Ser Gln Ile His His Ala Asp Ser Val Lys Gly
                50                  55                  60

Arg Phe Ser Ile Ser Lys Asp Asn Ala Lys Asn Ser Leu Tyr Leu Gln
            65                  70                  75                  80

Met Asn Ser Gln Arg Ala Glu Asp Met Asp Val Tyr Gly Cys Thr Gly
                            85                  90                  95

<210> SEQ ID NO 92
<211> LENGTH: 94
<212> TYPE: PRT
<213> ORGANISM: Homo sapiens

<400> SEQUENCE: 92

Glu Val Gln Leu Val Glu Ser Gly Glu Asp Pro Arg Gln Pro Gly Gly
            1               5                   10                  15

Ser Leu Arg Leu Ser Cys Ala Asp Ser Gly Leu Thr Phe Ser Ser Tyr
                            20                  25                  30

Arg Ser Ser Val Ser Gln Ala Pro Gly Lys Gly Leu Glu Val Val Asp
                        35                  40                  45

Ile Gln Cys Asp Gly Ser Gln Ile Cys Tyr Ala Ser Leu Lys Ser Lys
                50                  55                  60

Phe Thr Ile Ser Lys Glu Asn Ala Lys Asn Ser Leu Tyr Leu Leu Met
            65                  70                  75                  80

Asn Ser Leu Arg Ala Glu Gly Thr Ala Val Cys Tyr Cys Met
                            85                  90

<210> SEQ ID NO 93
<211> LENGTH: 96
<212> TYPE: PRT
<213> ORGANISM: Homo sapiens

<400> SEQUENCE: 93

Glu Val Glu Leu Ile Glu Pro Thr Glu Asp Leu Arg Gln Pro Gly Lys
            1               5                   10                  15

Phe Leu Arg Leu Ser Cys Val Ala Ser Arg Phe Ala Phe Ser Ser Phe
                            20                  25                  30

Met Ser Pro Val His Gln Ser Ala Gly Lys Gly Leu Glu Val Ile Asp
                        35                  40                  45

Ile Lys Asp Asp Gly Ser Gln Ile His His Ala Asp Ser Val Lys Gly
                50                  55                  60

Arg Phe Ser Ile Ser Lys Asp Asn Ala Lys Asn Ser Leu Tyr Leu Gln
            65                  70                  75                  80

Met Asn Ser Gln Arg Thr Glu Asp Met Ala Val Tyr Gly Cys Thr Gly
                            85                  90                  95

<210> SEQ ID NO 94
<211> LENGTH: 94
<212> TYPE: PRT
<213> ORGANISM: Homo sapiens

<400> SEQUENCE: 94

Glu Val Gln Leu Val Glu Ser Gly Glu Asp Pro Arg Gln Pro Gly Gly
            1               5                   10                  15
```

```
Ser Leu Arg Leu Ser Cys Ala Asp Ser Gly Leu Thr Phe Ser Ser Tyr
            20                  25                  30

Arg Asn Ser Val Ser Gln Ala Pro Gly Lys Gly Leu Glu Val Val Asp
        35                  40                  45

Ile Gln Cys Asp Gly Ser Gln Ile Cys Tyr Ala Ser Leu Lys Ser Lys
50                  55                  60

Phe Thr Ile Ser Lys Glu Asn Ala Lys Asn Ser Leu Tyr Leu Leu Met
65                  70                  75                  80

Asn Ser Leu Arg Ala Ala Gly Thr Ala Val Cys Tyr Cys Met
                85                  90

<210> SEQ ID NO 95
<211> LENGTH: 96
<212> TYPE: PRT
<213> ORGANISM: Homo sapiens

<400> SEQUENCE: 95

Glu Val Glu Leu Ile Glu Ser Ile Glu Asp Leu Arg Gln Pro Gly Lys
1               5                   10                  15

Phe Leu Arg Leu Ser Cys Val Ala Ser Arg Phe Ala Phe Ser Ser Phe
            20                  25                  30

Met Ser Arg Val His Gln Ser Pro Gly Lys Gly Leu Glu Val Ile Asp
        35                  40                  45

Ile Lys Asp Asp Gly Ser Gln Ile His His Ala Asp Ser Val Lys Gly
50                  55                  60

Arg Phe Ser Ile Ser Lys Asp Asn Ala Lys Asn Ser Leu Tyr Leu Gln
65                  70                  75                  80

Met Asn Thr Gln Arg Ala Glu Asp Val Ala Val Tyr Gly Tyr Thr Gly
                85                  90                  95

<210> SEQ ID NO 96
<211> LENGTH: 98
<212> TYPE: PRT
<213> ORGANISM: Homo sapiens

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 97
<211> LENGTH: 98
<212> TYPE: PRT
<213> ORGANISM: Homo sapiens

<400> SEQUENCE: 97

Gln Val Gln Leu Val Glu Ser Gly Gly Gly Val Val Gln Pro Gly Arg
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Ala
    50                  55                  60

Lys Gly Arg Phe Thr Ile Ser Arg Asp Asn Ser Thr Asn Thr Leu Phe
65                  70                  75                  80

Leu Gln Met Asn Ser Leu Arg Ala Glu Asp Thr Ala Val Tyr Tyr Cys
                85                  90                  95

Ala Arg

<210> SEQ ID NO 98
<211> LENGTH: 98
<212> TYPE: PRT
<213> ORGANISM: Homo sapiens

<400> SEQUENCE: 98

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 99
<211> LENGTH: 98
<212> TYPE: PRT
<213> ORGANISM: Homo sapiens

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 100
<211> LENGTH: 96
<212> TYPE: PRT
```

<213> ORGANISM: Homo sapiens

<400> SEQUENCE: 100

Glu Val Gln Leu Val Glu Ser Gly Glu Asp Pro Arg Gln Pro Gly Gly
1               5                   10                  15

Ser Leu Arg Leu Ser Cys Ala Asp Ser Gly Leu Thr Phe Ser Ser Tyr
            20                  25                  30

Met Ser Ser Val Ser Gln Ala Pro Gly Lys Gly Leu Glu Val Val Asp
        35                  40                  45

Ile Gln Cys Asp Gly Ser Gln Ile Cys Tyr Ala Gln Ser Val Lys Ser
    50                  55                  60

Lys Phe Thr Ile Ser Lys Glu Asn Ala Lys Asn Ser Leu Tyr Leu Gln
65                  70                  75                  80

Met Asn Ser Leu Arg Ala Glu Gly Thr Ala Val Cys Tyr Cys Met Gly
                85                  90                  95

<210> SEQ ID NO 101
<211> LENGTH: 98
<212> TYPE: PRT
<213> ORGANISM: Homo sapiens

<400> SEQUENCE: 101

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 102
<211> LENGTH: 98
<212> TYPE: PRT
<213> ORGANISM: Homo sapiens

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

```
<210> SEQ ID NO 103
<211> LENGTH: 98
<212> TYPE: PRT
<213> ORGANISM: Homo sapiens

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Val Arg

<210> SEQ ID NO 104
<211> LENGTH: 97
<212> TYPE: PRT
<213> ORGANISM: Homo sapiens

<400> SEQUENCE: 104

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Ala Tyr Tyr Cys Ala Arg
                85                  90                  95

Tyr

<210> SEQ ID NO 105
<211> LENGTH: 97
<212> TYPE: PRT
<213> ORGANISM: Homo sapiens

<400> SEQUENCE: 105

Glu Val Gln Leu Val Glu Ser Gly Gly Gly Leu Val Gln Pro Arg Gly
1               5                   10                  15

Ser Leu Arg Leu Ser Cys Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Val Tyr Tyr Cys Ala Arg
```

Tyr

<210> SEQ ID NO 106
<211> LENGTH: 97
<212> TYPE: PRT
<213> ORGANISM: Homo sapiens

<400> SEQUENCE: 106

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Thr Leu Tyr Leu Gln
65                  70                  75                  80

Met Asn Asn Leu Arg Ala Glu Gly Thr Ala Val Tyr Tyr Cys Ala Arg
                85                  90                  95

Tyr

<210> SEQ ID NO 107
<211> LENGTH: 96
<212> TYPE: PRT
<213> ORGANISM: Homo sapiens

<400> SEQUENCE: 107

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
                85                  90                  95

<210> SEQ ID NO 108
<211> LENGTH: 99
<212> TYPE: PRT
<213> ORGANISM: Homo sapiens

<400> SEQUENCE: 108

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr

```
                65                  70                  75                  80
Leu Gln Met Asn Ser Leu Arg Thr Glu Asp Thr Ala Leu Tyr Tyr Cys
                85                  90                  95

Ala Lys Asp

<210> SEQ ID NO 109
<211> LENGTH: 99
<212> TYPE: PRT
<213> ORGANISM: Homo sapiens

<400> SEQUENCE: 109

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Gly Asp Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 110
<211> LENGTH: 99
<212> TYPE: PRT
<213> ORGANISM: Homo sapiens

<400> SEQUENCE: 110

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Trp Asp Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 111
<211> LENGTH: 97
<212> TYPE: PRT
<213> ORGANISM: Homo sapiens

<400> SEQUENCE: 111

Glu Asp Gln Leu Val Glu Ser Gly Gly Gly Leu Val Gln Pro Gly Gly
1               5                   10                  15

Ser Leu Arg Pro Ser Cys Ala Ala Ser Gly Phe Ala Phe Ser Ser Tyr
                20                  25                  30

Ala Leu His Trp Val Arg Arg Ala Pro Gly Lys Gly Leu Glu Trp Val
            35                  40                  45
```

```
Ser Ala Ile Gly Thr Gly Gly Asp Thr Tyr Tyr Ala Asp Ser Val Met
        50                  55                  60

Gly Arg Phe Thr Ile Ser Arg Asp Asn Ala Lys Lys Ser Leu Tyr Leu
 65                  70                  75                  80

His Met Asn Ser Leu Ile Ala Glu Asp Met Ala Val Tyr Tyr Cys Ala
                85                  90                  95

Arg

<210> SEQ ID NO 112
<211> LENGTH: 97
<212> TYPE: PRT
<213> ORGANISM: Homo sapiens

<400> SEQUENCE: 112

Glu Asp Gln Leu Val Glu Ser Gly Gly Gly Leu Val Gln Pro Gly Gly
 1               5                  10                  15

Ser Leu Arg Pro Ser Cys Ala Ala Ser Gly Phe Ala Phe Ser Ser Tyr
                20                  25                  30

Val Leu His Trp Val Arg Arg Ala Pro Gly Lys Gly Pro Glu Trp Val
            35                  40                  45

Ser Ala Ile Gly Thr Gly Gly Asp Thr Tyr Tyr Ala Asp Ser Val Met
        50                  55                  60

Gly Arg Phe Thr Ile Ser Arg Asp Asn Ala Lys Lys Ser Leu Tyr Leu
 65                  70                  75                  80

Gln Met Asn Ser Leu Ile Ala Glu Asp Met Ala Val Tyr Tyr Cys Ala
                85                  90                  95

Arg

<210> SEQ ID NO 113
<211> LENGTH: 98
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 114
<211> LENGTH: 98
<212> TYPE: PRT
<213> ORGANISM: Homo sapiens

<400> SEQUENCE: 114

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 115
<211> LENGTH: 98
<212> TYPE: PRT
<213> ORGANISM: Homo sapiens

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 116
<211> LENGTH: 98
<212> TYPE: PRT
<213> ORGANISM: Homo sapiens

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 117
<211> LENGTH: 100
<212> TYPE: PRT
<213> ORGANISM: Homo sapiens

<400> SEQUENCE: 117

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 118
<211> LENGTH: 100
<212> TYPE: PRT
<213> ORGANISM: Homo sapiens

<400> SEQUENCE: 118

Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Thr Phe Gly Tyr Tyr
            20                  25                  30

Pro Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 119
<211> LENGTH: 100
<212> TYPE: PRT
<213> ORGANISM: Homo sapiens

<400> SEQUENCE: 119

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg

<210> SEQ ID NO 120
<211> LENGTH: 100
<212> TYPE: PRT
<213> ORGANISM: Homo sapiens

<400> SEQUENCE: 120

Glu Val Gln Leu Val Glu Ser Gly Gly Gly Leu Val Gln Pro Gly Arg
1               5                   10                  15
Ser Leu Arg Leu Ser Cys Thr Ala Ser Gly Phe Thr Phe Gly Asp Tyr
            20                  25                  30
Ala Met Ser Trp Val Arg Gln Ala Pro Gly Lys Gly Leu Glu Trp Val
        35                  40                  45
Gly Phe Ile Arg Ser Lys Ala Tyr Gly Gly Thr Thr Glu Tyr Ala Ala
    50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Lys Thr Glu Asp Thr Ala Val Tyr
                85                  90                  95
Tyr Cys Thr Arg
            100

<210> SEQ ID NO 121
<211> LENGTH: 100
<212> TYPE: PRT
<213> ORGANISM: Homo sapiens

<400> SEQUENCE: 121

Glu Val Gln Leu Val Glu Ser Gly Gly Gly Leu Val Lys Pro Gly Arg
1               5                   10                  15
Ser Leu Arg Leu Ser Cys Thr Ala Ser Gly Phe Thr Phe Gly Asp Tyr
            20                  25                  30
Ala Met Ser Trp Phe Arg Gln Ala Pro Gly Lys Gly Leu Glu Trp Val
        35                  40                  45
Gly Phe Ile Arg Ser Lys Ala Tyr Gly Gly Thr Thr Glu Tyr Ala Ala
    50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Lys Thr Glu Asp Thr Ala Val Tyr
                85                  90                  95
Tyr Cys Thr Arg
            100

<210> SEQ ID NO 122
<211> LENGTH: 97
<212> TYPE: PRT
<213> ORGANISM: Homo sapiens

<400> SEQUENCE: 122

Glu Val Gln Leu Val Glu Ser Gly Gly Leu Val Gln Pro Gly Gly Ser
1               5                   10                  15
Leu Arg Leu Ser Cys Ala Ala Ser Gly Phe Thr Phe Ser Ser Trp
            20                  25                  30
Met His Trp Val Cys Gln Ala Pro Glu Lys Gly Leu Glu Trp Val Ala
        35                  40                  45
Asp Ile Lys Cys Asp Gly Ser Glu Lys Tyr Tyr Val Asp Ser Val Lys
    50                  55                  60

Gly Arg Leu Thr Ile Ser Arg Asp Asn Ala Lys Asn Ser Leu Tyr Leu
65                  70                  75                  80

Gln Val Asn Ser Leu Arg Ala Glu Asp Met Thr Val Tyr Tyr Cys Val
                85                  90                  95

Arg

<210> SEQ ID NO 123
<211> LENGTH: 97
<212> TYPE: PRT
<213> ORGANISM: Homo sapiens

<400> SEQUENCE: 123

Glu Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser Ser Ser Trp
                20                  25                  30

Met His Trp Val Cys Gln Ala Pro Glu Lys Gly Gln Glu Trp Val Ala
            35                  40                  45

Asp Ile Lys Cys Asp Gly Ser Glu Lys Tyr Tyr Val Asp Ser Val Lys
        50                  55                  60

Gly Arg Leu Thr Ile Ser Arg Asp Asn Ala Lys Asn Ser Leu Tyr Leu
65                  70                  75                  80

Gln Val Asn Ser Leu Arg Ala Glu Asp Met Thr Val Tyr Tyr Cys Val
                85                  90                  95

Arg

<210> SEQ ID NO 124
<211> LENGTH: 97
<212> TYPE: PRT
<213> ORGANISM: Homo sapiens

<400> SEQUENCE: 124

Glu Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser Ser Ser Trp
                20                  25                  30

Met His Trp Val Cys Gln Ala Pro Glu Lys Gly Leu Glu Trp Val Ala
            35                  40                  45

Asp Ile Lys Cys Asp Gly Ser Glu Lys Tyr Tyr Val Asp Ser Val Lys
        50                  55                  60

Gly Arg Leu Thr Ile Ser Arg Asp Asn Ala Lys Asn Ser Leu Tyr Leu
65                  70                  75                  80

Gln Val Asn Ser Leu Arg Ala Glu Asp Met Thr Val Tyr Tyr Cys Val
                85                  90                  95

Arg

<210> SEQ ID NO 125
<211> LENGTH: 97
<212> TYPE: PRT
<213> ORGANISM: Homo sapiens

<400> SEQUENCE: 125

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 126
<211> LENGTH: 97
<212> TYPE: PRT
<213> ORGANISM: Homo sapiens

<400> SEQUENCE: 126

Glu Val Gln Leu Val Glu Thr Gly Gly Gly Leu Ile Gln Pro Gly Gly
 1               5                  10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 127
<211> LENGTH: 97
<212> TYPE: PRT
<213> ORGANISM: Homo sapiens

<400> SEQUENCE: 127

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                20                  25                  30

Tyr Met Ser Trp Val Arg Gln Pro Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 128
<211> LENGTH: 97
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly

```
              1               5                  10                 15
            Ser Leu Arg Leu Ser Cys Ala Ala Ser Gly Phe Thr Val Ser Ser Asn
                            20                  25                 30

Tyr Met Ser Trp Val Arg Gln Ala Pro Gly Lys Gly Leu Glu Trp Val
                            35                  40             45

Ser Val Ile Tyr Ser Gly Gly Ser Thr Tyr Tyr Ala Asp Ser Val Lys
                            50              55                  60

Gly Arg Phe Thr Ile Ser Arg His Asn Ser Lys Asn Thr Leu Tyr Leu
            65                  70                  75                  80

Gln Met Asn Ser Leu Arg Ala Glu Asp Thr Ala Val Tyr Tyr Cys Ala
                            85                  90                  95

Arg

<210> SEQ ID NO 129
<211> LENGTH: 93
<212> TYPE: PRT
<213> ORGANISM: Homo sapiens

<400> SEQUENCE: 129

Glu Val Gln Leu Val Glu Ser Glu Glu Asn Gln Arg Gln Leu Gly Gly
            1               5                   10                  15

Ser Leu Arg Leu Ser Cys Ala Asp Ser Gly Leu Thr Phe Ser Ser Tyr
                            20                  25                  30

Met Ser Ser Asp Ser Gln Ala Pro Gly Lys Gly Leu Glu Val Val Asp
                            35                  40                  45

Ile Asp Arg Ser Gln Leu Cys Tyr Ala Gln Ser Val Lys Ser Arg Phe
                            50              55                  60

Thr Ile Ser Lys Glu Asn Ala Lys Asn Ser Leu Cys Leu Gln Met Asn
            65                  70                  75                  80

Ser Leu Arg Ala Glu Gly Thr Ala Val Tyr Tyr Cys Met
                            85                  90

<210> SEQ ID NO 130
<211> LENGTH: 94
<212> TYPE: PRT
<213> ORGANISM: Homo sapiens

<400> SEQUENCE: 130

Glu Val Gln Leu Val Glu Ser Glu Glu Asn Gln Arg Gln Leu Gly Gly
            1               5                   10                  15

Ser Leu Arg Leu Ser Cys Ala Asp Ser Gly Leu Thr Phe Ser Ser Tyr
                            20                  25                  30

Met Ser Ser Asp Ser Gln Ala Pro Gly Lys Gly Leu Glu Val Val Asp
                            35                  40                  45

Ile Tyr Asp Arg Ser Gln Ile Cys Tyr Ala Gln Ser Val Lys Ser Arg
                            50              55                  60

Phe Thr Ile Ser Lys Glu Asn Ala Lys Asn Ser Leu Arg Leu Gln Met
            65                  70                  75                  80

Asn Ser Leu Arg Ala Glu Gly Thr Ala Val Tyr Tyr Cys Met
                            85                  90

<210> SEQ ID NO 131
<211> LENGTH: 93
<212> TYPE: PRT
<213> ORGANISM: Homo sapiens

<400> SEQUENCE: 131
```

```
Glu Val Gln Leu Val Glu Ser Glu Glu Asn Gln Arg Gln Leu Gly Gly
1               5                   10                  15

Ser Leu Arg Leu Ser Cys Ala Asp Ser Gly Leu Thr Phe Ser Ser Tyr
            20                  25                  30

Met Ser Ser Asp Ser Gln Ala Pro Gly Lys Gly Leu Glu Val Val Asp
        35                  40                  45

Ile Asp Arg Ser Gln Leu Cys Tyr Ala Gln Ser Val Lys Ser Arg Phe
50                  55                  60

Thr Ile Ser Lys Glu Asn Ala Lys Asn Ser Leu Cys Leu Gln Met Asn
65                  70                  75                  80

Ser Leu Arg Ala Glu Gly Thr Ala Val Tyr Tyr Cys Met
            85                  90
```

<210> SEQ ID NO 132
<211> LENGTH: 97
<212> TYPE: PRT
<213> ORGANISM: Homo sapiens

<400> SEQUENCE: 132

```
Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met His Trp Val Arg Gln Ala Pro Arg Lys Gly Leu Trp Val Ser
        35                  40                  45

Val Ile Ser Thr Ser Gly Asp Thr Val Leu Tyr Thr Asp Ser Val Lys
50                  55                  60

Gly Arg Phe Thr Ile Ser Arg Asp Asn Ala Gln Asn Ser Leu Ser Leu
65                  70                  75                  80

Gln Met Asn Ser Leu Arg Ala Glu Gly Thr Val Val Tyr Tyr Cys Val
            85                  90                  95

Lys
```

<210> SEQ ID NO 133
<211> LENGTH: 97
<212> TYPE: PRT
<213> ORGANISM: Homo sapiens

<400> SEQUENCE: 133

```
Glu Val Glu Leu Ile Glu Ser Ile Glu Gly Leu Arg Gln Leu Gly Lys
1               5                   10                  15

Phe Leu Arg Leu Ser Cys Val Ala Ser Gly Phe Thr Phe Ser Ser Tyr
            20                  25                  30

Met Ser Trp Val Asn Glu Thr Leu Gly Lys Gly Leu Glu Gly Val Ile
        35                  40                  45

Asp Val Lys Tyr Asp Gly Ser Gln Ile Tyr His Ala Asp Ser Val Lys
50                  55                  60

Gly Arg Phe Thr Ile Ser Lys Asp Asn Ala Lys Asn Ser Pro Tyr Leu
65                  70                  75                  80

Gln Thr Asn Ser Leu Arg Ala Glu Asp Met Thr Met His Gly Cys Thr
            85                  90                  95

Gly
```

<210> SEQ ID NO 134
<211> LENGTH: 96
<212> TYPE: PRT
<213> ORGANISM: Homo sapiens

<400> SEQUENCE: 134

Glu Val Glu Leu Ile Glu Ser Ile Glu Gly Leu Arg Gln Leu Gly Lys
1               5                   10                  15

Phe Leu Arg Leu Ser Cys Val Ala Ser Gly Phe Thr Phe Ser Ser Tyr
            20                  25                  30

Met Ser Trp Val Asn Glu Thr Leu Gly Lys Gly Leu Glu Gly Val Ile
        35                  40                  45

Asp Val Lys Tyr Asp Gly Ser Gln Ile Tyr His Ala Asp Ser Val Lys
    50                  55                  60

Gly Arg Phe Thr Ile Ser Lys Asp Asn Ala Lys Asn Ser Pro Tyr Leu
65                  70                  75                  80

Gln Thr Asn Ser Leu Arg Ala Glu Asp Met Thr Met His Gly Cys Thr
                85                  90                  95

<210> SEQ ID NO 135
<211> LENGTH: 98
<212> TYPE: PRT
<213> ORGANISM: Homo sapiens

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 136
<211> LENGTH: 98
<212> TYPE: PRT
<213> ORGANISM: Homo sapiens

<400> SEQUENCE: 136

Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 137

<211> LENGTH: 98
<212> TYPE: PRT
<213> ORGANISM: Homo sapiens

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys

<210> SEQ ID NO 138
<211> LENGTH: 98
<212> TYPE: PRT
<213> ORGANISM: Homo sapiens

<400> SEQUENCE: 138

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 139
<211> LENGTH: 98
<212> TYPE: PRT
<213> ORGANISM: Homo sapiens

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys

<210> SEQ ID NO 140
<211> LENGTH: 98
<212> TYPE: PRT
<213> ORGANISM: Homo sapiens

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys

<210> SEQ ID NO 141
<211> LENGTH: 97
<212> TYPE: PRT
<213> ORGANISM: Homo sapiens

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 142
<211> LENGTH: 97
<212> TYPE: PRT
<213> ORGANISM: Homo sapiens

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 143
<211> LENGTH: 97
<212> TYPE: PRT
<213> ORGANISM: Homo sapiens

<400> SEQUENCE: 143

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Cys Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 144
<211> LENGTH: 97
<212> TYPE: PRT
<213> ORGANISM: Homo sapiens

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 145
<211> LENGTH: 97
<212> TYPE: PRT
<213> ORGANISM: Homo sapiens

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val

```
                35                  40                  45

Ser Ser Ile Ser Ser Ser Thr Ile Tyr Tyr Ala Asp Ser Val Lys
         50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 146
<211> LENGTH: 97
<212> TYPE: PRT
<213> ORGANISM: Homo sapiens

<400> SEQUENCE: 146

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Asn Trp Val Arg Gln Ala Pro Gly Lys Gly Leu Glu Trp Val
             35                  40                  45

Ser Ser Ile Ser Ser Ser Thr Ile Tyr Tyr Ala Asp Ser Val Lys
         50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 147
<211> LENGTH: 99
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Val Arg Gln Ala Pro Gly Lys Gly Leu Glu Trp Val
             35                  40                  45

Gly Phe Ile Arg Asn Lys Ala Asn Gly Gly Thr Thr Glu Thr Thr Ser
         50                  55                  60

Val Lys Gly Arg Phe Thr Ile Ser Arg Asp Asp Ser Lys Ser Ile Thr
 65                  70                  75                  80

Tyr Leu Gln Met Asn Ser Leu Arg Ala Glu Asp Thr Ala Val Tyr Tyr
                 85                  90                  95

Cys Ala Arg

<210> SEQ ID NO 148
<211> LENGTH: 99
<212> TYPE: PRT
<213> ORGANISM: Homo sapiens

<400> SEQUENCE: 148

Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Gly Thr Thr Glu Thr Thr Ser
    50                  55                  60

Val Lys Gly Arg Phe Thr Ile Ser Arg Asp Asp Ser Lys Ser Ile Thr
65                  70                  75                  80

Tyr Leu Gln Met Asn Ser Leu Arg Ala Glu Asp Met Ala Val Tyr Tyr
                85                  90                  95

Cys Ala Arg
```

<210> SEQ ID NO 149
<211> LENGTH: 99
<212> TYPE: PRT
<213> ORGANISM: Homo sapiens

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Gly Thr Thr Glu Thr Thr Ser
    50                  55                  60

Val Lys Gly Arg Phe Thr Ile Ser Arg Asp Asp Ser Lys Ser Ile Thr
65                  70                  75                  80

Tyr Leu Gln Met Asn Ser Leu Arg Ala Glu Asp Thr Ala Val Tyr Tyr
                85                  90                  95

Cys Ala Arg
```

<210> SEQ ID NO 150
<211> LENGTH: 100
<212> TYPE: PRT
<213> ORGANISM: Homo sapiens

<400> SEQUENCE: 150

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100
```

<210> SEQ ID NO 151
<211> LENGTH: 55
<212> TYPE: PRT

<213> ORGANISM: Homo sapiens

<400> SEQUENCE: 151

Thr Phe Ser Asp His Tyr Met Asp Trp Val Arg Gln Ala Pro Gly Lys
1               5                   10                  15
Gly Leu Glu Trp Val Gly Arg Thr Arg Asn Lys Ala Asn Ser Tyr Thr
            20                  25                  30
Thr Glu Tyr Ala Ala Ser Val Lys Gly Arg Phe Thr Ile Ser Arg Asp
        35                  40                  45
Asp Ser Lys Asn Ser Leu Tyr
    50                  55

<210> SEQ ID NO 152
<211> LENGTH: 100
<212> TYPE: PRT
<213> ORGANISM: Homo sapiens

<400> SEQUENCE: 152

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Gly Ser
            20                  25                  30
Ala Met His Trp Val Arg Gln Ala Ser Gly Lys Gly Leu Glu Trp Val
        35                  40                  45
Gly Arg Ile Arg Ser Lys Ala Asn Ser Tyr Ala Thr Ala Tyr Ala Ala
    50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Arg
            100

<210> SEQ ID NO 153
<211> LENGTH: 100
<212> TYPE: PRT
<213> ORGANISM: Homo sapiens

<400> SEQUENCE: 153

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Gly Ser
            20                  25                  30
Ala Met His Trp Val Arg Gln Ala Ser Gly Lys Gly Leu Glu Trp Val
        35                  40                  45
Gly Arg Ile Arg Ser Lys Ala Asn Ser Tyr Ala Thr Ala Tyr Ala Ala
    50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Arg
            100

<210> SEQ ID NO 154
<211> LENGTH: 98
<212> TYPE: PRT
<213> ORGANISM: Homo sapiens

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 155
<211> LENGTH: 98
<212> TYPE: PRT
<213> ORGANISM: Homo sapiens

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 156
<211> LENGTH: 98
<212> TYPE: PRT
<213> ORGANISM: Homo sapiens

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 157
<211> LENGTH: 98
<212> TYPE: PRT
<213> ORGANISM: Homo sapiens

<400> SEQUENCE: 157

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Val Ile Tyr Ser Gly Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```